US007741054B2

(12) United States Patent
Eberle et al.

(10) Patent No.: US 7,741,054 B2
(45) Date of Patent: Jun. 22, 2010

(54) HIGH THROUGHPUT PRION ASSAYS

(75) Inventors: Walter Eberle, Bernried (DE); Werner Stock, Graefelfing (DE); Baerbel Winter, Tutzing (DE)

(73) Assignee: Roche Diagnostics, Operations, Inc., Indianapolis, IN (US)

( * ) Notice: Subject to any disclaimer, the term of this patent is extended or adjusted under 35 U.S.C. 154(b) by 216 days.

(21) Appl. No.: 11/273,487

(22) Filed: Nov. 14, 2005

(65) Prior Publication Data

US 2006/0121507 A1 Jun. 8, 2006

(30) Foreign Application Priority Data

Nov. 15, 2004 (EP) .................................. 04027088

(51) Int. Cl.
*G01N 33/48* (2006.01)
*C12Q 1/37* (2006.01)

(52) U.S. Cl. .......................................... 435/7.1; 435/23

(58) Field of Classification Search ....................... None
See application file for complete search history.

(56) References Cited

FOREIGN PATENT DOCUMENTS

WO 02/093164 A2 11/2002

OTHER PUBLICATIONS

Serban et al. (1990) Neurology. 40: 110-117.*
Yu and Cohen. (2004) LC-GC Europe. 2-6.*
Lane et al (2003) Clinical Chemistry. 49 (10): 1774-1777.*
Lee et al (1984) Zhonghua Min Guo Wei Sheng Wu Ji Mian Yi Xue Za Zhi-Abstract. 17(1): 36-47.*
Ardelt, W. et al., "Turkey Ovomucoid THird Domain Inhibits Eight Different Serine Proteinases of Varied Specificity on the Same . . . Leu18-Glu19 . . . Reactive Site," Biochemistry 1985, 24, 5313-5320.

* cited by examiner

*Primary Examiner*—Zachariah Lucas
*Assistant Examiner*—Michelle Horning
(74) *Attorney, Agent, or Firm*—Marilyn Amick; Roche Diagnostics Operations, Inc.

(57) ABSTRACT

The invention is directed to a method for performing a high throughput test to determine the presence of PrPsc in a tissue sample taken post mortem from brain, the test comprising the workflow of (A) sample preparation, (B) sample treatment, (C) sample analysis, (D) controls, and (E) classifying the results of the analysis as positive or negative. The invention is further directed to preparing a treated biological sample suspected of containing PrPsc such that it is suitable for specific detection of PrPsc, if present, the method comprising the steps of (a) homogenizing the sample; followed by (b) digesting the sample proteolytically by adding to the homogenate Proteinase K and incubating the sample; followed by (c) adding a peptidic protease inhibitor to the incubated mixture of step (b), thereby obtaining a treated biological sample suitable for specific detection of PrPsc, if present. The invention further provides a conditioned microwell plate. In addition, the invention provides a soluble fusion protein comprising one or more epitopes of prion protein as well as a carrier polypeptide.

4 Claims, 13 Drawing Sheets

A

B

SEQUENCE LISTING

<160> NUMBER OF SEQ ID NOS: 5

<210> SEQ ID NO 1
<211> LENGTH: 196
<212> TYPE: PRT
<213> ORGANISM: Escherichia coli
<220> FEATURE:
<221> NAME/KEY: MISC_FEATURE
<222> LOCATION: (1)..(196)
<223> OTHER INFORMATION: FKBP-type peptidyl-prolyl cis-trans isomerase (rotamase); slyD gene product of Escherichia coli K12

<400> SEQUENCE: 1

```
Met Lys Val Ala Lys Asp Leu Val Val Ser Leu Ala Tyr Gln Val Arg
1               5                   10                  15

Thr Glu Asp Gly Val Leu Val Asp Glu Ser Pro Val Ser Ala Pro Leu
            20                  25                  30

Asp Tyr Leu His Gly His Gly Ser Leu Ile Ser Gly Leu Glu Thr Ala
        35                  40                  45

Leu Glu Gly His Glu Val Gly Asp Lys Phe Asp Val Ala Val Gly Ala
    50                  55                  60

Asn Asp Ala Tyr Gly Gln Tyr Asp Glu Asn Leu Val Gln Arg Val Pro
65                  70                  75                  80

Lys Asp Val Phe Met Gly Val Asp Glu Leu Gln Val Gly Met Arg Phe
                85                  90                  95

Leu Ala Glu Thr Asp Gln Gly Pro Val Pro Val Glu Ile Thr Ala Val
            100                 105                 110

Glu Asp Asp His Val Val Val Asp Gly Asn His Met Leu Ala Gly Gln
        115                 120                 125

Asn Leu Lys Phe Asn Val Glu Val Val Ala Ile Arg Glu Ala Thr Glu
    130                 135                 140

Glu Glu Leu Ala His Gly His Val His Gly Ala His Asp His His His
145                 150                 155                 160

Asp His Asp His Asp Gly Cys Cys Gly Gly His Gly His Asp His Gly
                165                 170                 175

His Glu His Gly Gly Glu Gly Cys Cys Gly Gly Lys Gly Asn Gly Gly
            180                 185                 190

Cys Gly Cys His
        195
```

<210> SEQ ID NO 2
<211> LENGTH: 23
<212> TYPE: PRT
<213> ORGANISM: Artificial sequence
<220> FEATURE:
<223> OTHER INFORMATION: (GGGS)5-GGG linker sequence

<400> SEQUENCE: 2

```
Gly Gly Gly Ser Gly Gly Gly Ser Gly Gly Gly Ser Gly Gly Gly Ser
1               5                   10                  15

Gly Gly Gly Ser Gly Gly Gly
            20
```

<210> SEQ ID NO 3
<211> LENGTH: 253
<212> TYPE: PRT
<213> ORGANISM: Homo sapiens
<220> FEATURE:
<221> NAME/KEY: MISC_FEATURE -continued
<222> LOCATION: (1)..(253)
<223> OTHER INFORMATION: Prion protein, preproprotein [Homo sapiens].

<400> SEQUENCE: 3

Met Ala Asn Leu Gly Cys Trp Met Leu Val Leu Phe Val Ala Thr Trp
1               5                   10                  15

Ser Asp Leu Gly Leu Cys Lys Lys Arg Pro Lys Pro Gly Gly Trp Asn
            20                  25                  30

Thr Gly Gly Ser Arg Tyr Pro Gly Gln Gly Ser Pro Gly Gly Asn Arg
        35                  40                  45

Tyr Pro Pro Gln Gly Gly Gly Gly Trp Gly Gln Pro His Gly Gly Gly
    50                  55                  60

Trp Gly Gln Pro His Gly Gly Gly Trp Gly Gln Pro His Gly Gly Gly
65                  70                  75                  80

Trp Gly Gln Pro His Gly Gly Gly Trp Gly Gln Gly Gly Gly Thr His
                85                  90                  95

Ser Gln Trp Asn Lys Pro Ser Lys Pro Lys Thr Asn Met Lys His Met
            100                 105                 110

Ala Gly Ala Ala Ala Ala Gly Ala Val Val Gly Gly Leu Gly Gly Tyr
        115                 120                 125

Val Leu Gly Ser Ala Met Ser Arg Pro Ile Ile His Phe Gly Ser Asp
    130                 135                 140

Tyr Glu Asp Arg Tyr Tyr Arg Glu Asn Met His Arg Tyr Pro Asn Gln
145                 150                 155                 160

Val Tyr Tyr Arg Pro Met Asp Glu Tyr Ser Asn Gln Asn Asn Phe Val
                165                 170                 175

His Asp Cys Val Asn Ile Thr Ile Lys Gln His Thr Val Thr Thr Thr
            180                 185                 190

Thr Lys Gly Glu Asn Phe Thr Glu Thr Asp Val Lys Met Met Glu Arg
        195                 200                 205

Val Val Glu Gln Met Cys Ile Thr Gln Tyr Glu Arg Glu Ser Gln Ala
    210                 215                 220

Tyr Tyr Gln Arg Gly Ser Ser Met Val Leu Phe Ser Ser Pro Pro Val
225                 230                 235                 240

Ile Leu Leu Ile Ser Phe Leu Ile Phe Leu Ile Val Gly
                245                 250

<210> SEQ ID NO 4
<211> LENGTH: 8
<212> TYPE: PRT
<213> ORGANISM: Artificial sequence
<220> FEATURE:
<223> OTHER INFORMATION: Histidine-tag (His-tag) sequence

<400> SEQUENCE: 4

Leu Glu His His His His His His
1               5

<210> SEQ ID NO 5
<211> LENGTH: 1761
<212> TYPE: DNA
<213> ORGANISM: Artificial sequence
<220> FEATURE:
<223> OTHER INFORMATION: tandem-EcSlyD and hPrP(23-230)

-continued

```
<400> SEQUENCE: 5

catatgaaag tagcaaaaga cctggtggtc agcctggcct atcaggtacg tacagaagac      60

ggtgtgttgg ttgatgagtc tccggtgagt gcgccgctgg actacctgca tggtcacggt     120

tccctgatct ctggcctgga aacggcgctg gaaggtcatg aagttggcga caaatttgat     180

gtcgctgttg gcgcgaacga cgcttacggt cagtacgacg aaaacctggt gcaacgtgtt     240

cctaaagacg tatttatggg cgttgatgaa ctgcaggtag gtatgcgttt cctggctgaa     300

accgaccagg gtccggtacc ggttgaaatc actgcggttg aagacgatca cgtcgtggtt     360

gatggtaacc acatgctggc cggtcagaac ctgaaattca acgttgaagt tgtggcgatt     420

cgcgaagcga ctgaagaaga actggctcat ggtcacgttc acggcgcgca cgatcaccac     480

cacgatcacg accacgacgg tggcggttcc ggcggtggct ctggtggcgg aagcggtggc     540

ggttccggcg gtggctctgg tggcggtaaa gtagcaaaag acctggtggt cagcctggcc     600

tatcaggtac gtacagaaga cggtgtgttg gttgatgagt ctccggtgag tgcgccgctg     660

gactacctgc atggtcacgg ttccctgatc tctggcctgg aaacggcgct ggaaggtcat     720

gaagttggcg acaaatttga tgtcgctgtt ggcgcgaacg acgcttacgg tcagtacgac     780

gaaaacctgg tgcaacgtgt tcctaaagac gtatttatgg gcgttgatga actgcaggta     840

ggtatgcgtt tcctggctga aaccgaccag ggtccggtac cggttgaaat cactgcggtt     900

gaagacgatc acgtcgtggt tgatggtaac cacatgctgg ccggtcagaa cctgaaattc     960

aacgttgaag ttgtggcgat tcgcgaagcg actgaagaag aactggctca tggtcacgtt    1020

cacggcgcgc acgatcacca ccacgatcac gaccacgacg gtggcggttc cggcggtggc    1080

tctggtggcg gatccggtgg cggttccggc ggtggctctg gtggcggtat gaaaaaaacgc   1140

ccaaaaccgg gtggctggaa cactgggggc agccgctatc ctggccaggg ctcgccggga    1200

gggaatcgtt acccaccaca gggtggtggg ggctggggtc agccgcacgg cggcggttgg    1260

gggcaaccgc atggcggcgg atggggtcaa cctcacgggg gaggctgggg ccaaccgcat    1320

ggtggtgggt ggggtcaggg aggcggtacg cattcccaat ggaacaaacc gagtaaaccc    1380

aaaaccaaca tgaagcatat ggcgggtgcc gctgccgcag gtgcagttgt cggtggcctg    1440

ggcggctaca tgttaggaag cgcgatgtca agacccatta tccattttgg ctctgactat    1500

gaagatcgtt actaccgcga gaatatgcac cgttatccga atcaggtgta ttatcgtccg    1560

atggatgaat acagcaacca gaataacttc gtccacgact gtgttaatat taccattaag    1620

cagcatacag tgacgacaac cacgaaaggt gaaaacttta ccgagaccga tgtgaaaatg    1680

atggaacgag tagtagaaca aatgtgcatc actcagtacg aacgcgagag tcaggcgtat    1740

tatcagcggg gctcgctcga g                                              1761
```

HIGH THROUGHPUT PRION ASSAYS

RELATED APPLICATIONS

This application claims priority to European patent application EP 04027088.6 filed Nov. 17, 2004.

FIELD OF THE INVENTION

The present invention deals with prion assays analyzing brain samples collected post mortem from animals or humans. A partially automated high throughput workflow is an embodiment of the invention. A particular embodiment is directed to synchronizing sample processing. Another embodiment is directed to time-saving processes when analyzing large numbers of samples and measures to preserve a high level of test accuracy. A further embodiment is directed to enhancing laboratory safety while processing large numbers of prion-infected sample material. Additionally, an embodiment is directed to an algorithm to calculate a cut-off value, in order to group the test results into distinct classes.

BACKGROUND OF THE INVENTION

Variant Creutzfeldt-Jakob disease (vCJD) is a rare and fatal human neurodegenerative condition. As with Creutzfeldt-Jakob disease, vCJD is classified as a transmissible spongiform encephalopathy (TSE) because of characteristic spongy degeneration of the brain and its ability to be transmitted. vCJD is a new disease that was first described in March, 1996. In contrast to the traditional forms of CJD, vCJD has affected younger patients (average age 29 years, as opposed to 65 years), has a relatively longer duration of illness (median of 14 months as opposed to 4.5 months) and is strongly linked to exposure, probably through food, to a TSE of cattle called Bovine spongiform encephalopathy (BSE). TSEs are also known in other animals. For instance, scrapie affects sheep and goats and has been found in many sheep-producing countries throughout the world for over 250 years. Chronic wasting disease (CWD) is a contagious fatal TSE in cervids (members of the deer and elk family).

The hypothesis of a link between vCJD and BSE was first raised because of the association of these two TSEs in time and place. More recent evidence supporting a link includes identification of pathological features similar to vCJD in brains of macaque monkeys inoculated with BSE. A vCJD-BSE link is further supported by the demonstration that vCJD is associated with a molecular marker that distinguishes it from other forms of CJD and which resembles that seen in BSE transmitted to a number of other species. Studies of the distribution of the infectious agent in the brains of mice artificially infected with tissues from humans with vCJD and cows with BSE showed nearly identical patterns. The most recent and powerful evidence comes from studies showing that the transmission characteristics of BSE and vCJD in laboratory mice are almost identical, strongly indicating that they are due to the same causative agent. In conclusion, the most likely cause of vCJD is exposure to the BSE agent, most plausibly due to dietary contamination by affected bovine central nervous system tissue.

The infectious agents involved in TSE are usually referred to as prions. These pathogens are characterized by unusual properties and, in particular, by their strong resistance to common procedures of disinfection used against conventional microorganisms. Prions that cause BSE in cattle and vCJD in humans are transmitted through infected food products. While the incubation period of the disease is quite long, the onset of symptoms leads to extreme neurological debilitation within a few months. All animals possess normal prion proteins, which are known by a variety of acronyms in the scientific literature, e.g., PrP or PrPc. PrPc are found on the surface of many cell types including nerves, lymphocytes, and macrophages. All proteins "fold" themselves into specific three-dimensional shapes. Sometimes normal prion proteins become abnormally folded. Then the abnormal prions can "infect" normal ones by physical contact in which the abnormally-folded prion causes the normal one also to become misfolded, thus spreading the diseased state.

A major component of highly infectious prion protein fractions is a Proteinase K-resistant prion protein, termed PrPsc. The normal host prion protein PrPc is sensitive to Proteinase K. The biochemical behavior of PrPsc under denaturing conditions and in the presence of Proteinase K provides a biochemical means for assaying the presence of PrPsc in tissue samples, thereby diagnosing TSE disease. Identification of infected farm animals such as cattle or sheep post mortem is of particular importance in order to prevent potentially hazardous meat and other products from entering the human food chain. As the number of animals slaughtered and processed by the meat industry is high, TSE assays which are to be performed by foodstuff monitoring centers and reference laboratories have to meet the needs of high throughput testing.

A general workflow to assay for TSE essentially comprises the following steps:

(1) Removing sample tissue from a sacrificed animal
- In the exemplary case of BSE the sample is preferably a piece of brain; usually, a part of the brain stem is removed when the animal is cut up. Preferably, the piece of brain includes the obex. However, other tissues are possible including spinal chord tissue and also lymph node or tonsil tissue.

(2) Taking a defined amount of tissue, which in the following will be referred to as "the sample", "the sampled tissue", or "the tissue sample"

(3) Homogenizing th tissue sample (4) Treating the homogenized sample such that it is suitable for specific detection of PrPsc, if present
- A preferred pretreatment uses proteolytic digestion of the homogenized sample with Proteinase K and denaturation with a chaotropic agent.

(5) Incubating the treated sample with one or more specific binding agents
- Usually the binding agent is an antibody or an antibody fragment. The amount of complex formed by the binding agent(s) and the analyte is measured to result in a measurement value. In case a sample treated with Proteinase K and chaotropic agent is analyzed, the binding agents are specific for a fragment of PrPsc which resists the Proteinase K treatment.

(6) In order to assign a quantitative value to a positive or negative test result, using an algorithm which takes into account reference data and/or measurement values generated in one or more control experiments The present invention focuses on steps (3), (4), (5) and (6) of the workflow. Step (5) according to the invention includes pretreatment with a proteolytic enzyme and chaotropic agent.

With respect to commercialized test systems, there exist several ways of performing steps (3) to (6). Generally, the processing of infective tissue often requires complex equipment in order to fulfill the needs of laboratory safety on the one hand and technical requirements on the other.

A first test system developed by Prionics AG (Schlieren, Switzerland) is distributed under the commercial name PRI- ONICS-Check WESTERN and PRIONICS-Check LIA (=luminescence immunoassay, described further below). The PRIONICS-Check LIA test system comprises (i) homogenization of sample tissue using a complex device and apparatus, (ii) proteolytic sample treatment, and (iii) immunological detection of PrPsc, whereby steps (ii) and (iii) are performed in the 96-well format.

According to the user's manual of the test system, for the homogenization step a deconstituting device for the preparation of biological samples as described in WO 02/48679 is used. The device comprises a container in the form of a cup for holding the tissue to be deconstituted. A shaft is mounted for rotation inside the container with a blade on the end inside the container. The shaft is supported axially by ball coupling means and has engagement means on its end outside the container for coupling the shaft to a motor. The device is used in an automatic apparatus (FASTH PCPM4, cod. 80040, Consul A R, Villeneuve, Switzerland), which includes at least one support element with a plurality of housings for receiving the container; a deconstitution station which includes at least one motor with a drive shaft for engaging the engagement means of the shaft of the deconstituting device, whereby the motor is movable between a position disengaged from the shaft and one position engaging it; and conveyor means for transporting the support element to the deconstitution station. The FASTH device simultaneously processes 4 containers which are placed in a rack. The rack takes up eight containers which are processed in two subsequent steps. Another device (MEDIFASTH, Consul) is commercially available which works similarly but processes only two containers at a time. The containers are placed in racks, whereby each rack takes up two containers.

The containers are commercially available as disposable items (PRYPCONS, Consul A R, Villeneuve, Switzerland) made of plastic. Each container has a sliding gate in the lid through which the sampled brain tissue is transferred into the container. The FASTH device is capable of taking up and subsequently processing 6 racks, i.e., 48 containers. Racks with processed containers can be removed from the running device; similarly, the device can be loaded with new racks. According to the manufacturer the device is capable of homogenizing up to 250 samples/h.

In each container a sample of 350-700 mg of tissue is homogenized together with a ten-fold volume of homogenization buffer. In order to ensure a proper sample vs. buffer ratio, the weight of the sample tissue is determined before. Following the homogenization process, an aliquot of the homogenate (1 ml) is taken manually from the container, usually with a hand pipet using disposable pipet tips, and is transferred to a 96-well "sample master plate". Alternatively, the homogenate can be removed and transferred by means of an automatic pipetting device (e.g., supplied by TECAN Group Ltd., Switzerland). However, the sliding gate of each container has to be opened manually.

In a cavity of a microwell plate (the "digestion" plate), a volume of 100 μl of the homogenate is mixed with 50 μl of a digestion solution containing a protease. The mixture is then sealed and incubated. Following an incubation, 10 μl of a stop solution are added to the digested homogenate and mixed. A volume of 15 μl of the mixture is transferred to a cavity of another microwell plate (the "preincubation plate") which contains 15 μl of an "assay buffer". Transfer and mixing of samples with assay buffer have to be completed within 2-5 min. After 2-5 min a volume of 10 μl "preincubation buffer" is added, mixed, and incubated for about 2 min. Subsequently, 200 μl of "detection antibody solution" are added and mixed. The plate is sealed and incubated on a shaker for about 60 min. Subsequently, a volume of 200 μl of each cavity is transferred to the corresponding cavity of a "capture plate". The plate is then incubated for about 90 min on a shaker. After that, the capture plate is washed with wash buffer four times using an ELISA washer. Remaining liquid is removed (preferably by clapping), and each cavity is filled with 100 μl of a chemiluminescent substrate working solution. After an incubation period of 5-10 min, the light signals are read in a chemiluminometer, and the signals are recorded.

A different test system is the Enfer TSE diagnostic kit which is distributed by Abbott Laboratories, USA. The homogenization method depends on the Stomacher apparatus (Seward Stomacher 80). The apparatus provides a mechanical action in which contoured paddles apply pressure to a sample bag. Sample tissue in the sample bag is subjected to homogenization in the presence of a sample buffer. This method is suited for soft tissue such as obex. A single apparatus is capable of processing 2 bags at a time. Homogenization of a tissue sample typically takes 2 min. For each single sample preparation a new blade, tongue depressor, weighing boat, and homogenizer bag must be used to prevent cross-contamination. The tissue sample is a thin cross-section of CNS tissue weighing between at least 0.5 g and 1.0 g. Weighing and transferring the sample into the bag require extensive manual work. Per 1 g of tissue, 15 ml of sample buffer are added into the bag. When dispensing the sample buffer, care must be taken to avoid contact of the dispenser with the bag. Homogenization is controlled by visual inspection. After the homogenization step, the homogenizer bag is left between 5 min and 40 min to allow bubbles to subside.

Following the homogenization process, the homogenization bag is opened and an aliquot (180 μl) of the liquid homogenate is taken manually out of the bag with a hand pipet using disposable pipet tips. At this point care must be taken not to allow the pipette to be contaminated on the outside by material from the homogenizer bag. The homogenate is transferred to a 96-well microwell plate. The plate is sealed and subjected to centrifugation at 4,000×g at room temperature for 5 min. One hundred μl of the supernatant are then transferred to a second 96-well microwell plate containing 20 μl of a Proteinase K solution. According to the user's manual, the Proteinase K solution has a tendency to stick to the side of the cavities. In order to prevent this, the buffer has to be pipetted to the very bottom of the cells. When transferring the supernatant, care must be taken not to disturb the pellet because transfer of solid particles must be prevented. The plate is then covered with a plate sealer, and samples are then incubated for 60 min on a shaker. During this step, PrPsc aggregates are hydrophobically bound to the cavities of the microwell plate while the Proteinase K digests away the PrPc, thus allowing the distinction of PrPsc from PrPc. The pipetting steps of this protocol can be automated.

The cavities of the microwell plate are washed, and the plate is clapped to remove remaining liquid. Subsequently, the sample cavities are incubated with 150 μl of Enfer buffer 3 for 15 min. The plate is washed again, clapped, and after that, rabbit polyclonal antibody specific for the PrP protein in a volume of 150 μl is added to the cavities. The plate is sealed again and incubated for 40 min. After that, the cavities are washed again and then incubated with an enzyme-conjugated second antibody. After incubation with the conjugate, the cavities are washed, and chemiluminescent substrate is added. The light signal is read in a chemiluminometer and the signal is recorded.

Another commercially available test system is the TeSeE BSE test distributed by Bio-Rad Laboratories (Munich, Germany; catalogue numbers 3551144 [purification kit], 3551145 [detection kit], 3551120 [calibration syringe and needle]). This method is adapted for processing two times 45 samples (plus controls) at a time, whereby in the beginning test tubes in racks in the 6*8 format are used.

An amount of 350 μg±40 μg of brain stem tissue, preferred obex tissue, is transferred to a grinding tube. This is a test vial with a volume of about 2 ml containing about 1.5 ml homogenization buffer and grinding beads. Test vials pre-filled with beads and buffer are part of the Bio-Rad kit. The grinding beads have a diameter of between 0.5 mm and 1 mm. The tube is filled with grinding beads up to about the 200 μl marking. Upon transfer of sample tissue, each test vial is closed manually with a screw cap, and the vial is placed in a rack which holds 48 vials in total. The homogenization step is performed by using a RIBOLYSER or a TeSeE Precess 48 device. Basically, the device agitates the racks with the vials, and the movement of the beads in each vial homogenizes the sample tissue contained therein.

Following the homogenization step, the rack is removed from the agitation device, each vial is opened manually, and a volume of 250 μl of the homogenate is removed using a syringe for single use which is fitted with a calibrated blunt end needle. The needle needs to be immersed in the pellet of beads to avoid taking up poorly homogenized tissue fragments.

The homogenates are transferred to reaction vials for further treatment. An equal volume of Proteinase K solution is added, mixed, and incubated at 37° C. for 10 min. Mixing is done manually by inverting the tubes 10 times. According to the user's manual, the time between adding Proteinase K solution and the incubation at 37° C. must not exceed 2 min. After the incubation, a volume of 250 μl of a "clarifying solution" (reagent B) is added and mixed. It is noted that for this step, the Eppendorf vial has to be manually opened and closed again. It is also noted that according to the user's manual, the time after the incubation until the point when the clarifying solution is mixed must not exceed 2 min. Within 30 min, the Eppendorf reaction vials are centrifuged for 5 min at 20,000×g. The vials are opened again, and the supernatants are discarded. The vials are dried by inverting onto absorbent paper for 5 min. Subsequently, a volume of 25 μl of "resolving buffer" (reagent C) is added to each vial, the vial is closed again and then immediately incubated at 100° C. for 5 min. After that, in another manual step, the vials are agitated on a vortex mixer for 5 seconds.

The treated sample is then diluted with 125 μl PBS containing BSA and mixed by vortexing just before transfer to a microwell plate. One hundred μl of the diluted sample are transferred to the microwell plate which is coated with a monoclonal capture antibody. The plate is sealed with adhesive tape. After incubation of the plate for about 75 min at 37° C., the plate is washed using an automatic washer, and subsequently 100 μl of a solution containing an enzyme-conjugated detection antibody are added to each cavity. The plate is sealed again with adhesive tape. After incubation of the plate for about 1 h, the plate is washed again, and a volume of 100 μl of a substrate solution is added to each cavity. After 30 min, the enzyme reaction is stopped by adding a stop solution. Signals are read in a microwell plate reader, and the signals are recorded.

The methods of the state of the art have certain disadvantages. Particularly the homogenization process represents a bottleneck with regard to both susceptibility to contamination and sample throughput. It is noted that a test system which would be performed entirely in the standardized 8×12 (i.e., 96-well) format would be advantageous. Also, a cost-effective workflow in this format with reduced hands-on time is desired.

For the PRYPCON container it is noted that the tissue is homogenized in the container in the presence of a homogenization buffer by means of fast rotating (20,000 r.p.m.) blades. As a consequence, an aerosol containing components of possibly prion-infected brain tissue is generated in the airspace in the inner compartment of the container. Regarding the container it is noted in addition that both (i) the opening of the lid with the shaft inserted and (ii) the sliding gate do not provide completely airtight (i.e., pressure-tight) sealing of the inner compartment where the homogenization takes place. The sample bags used for homogenization with the Stomacher apparatus may also give rise to contamination, particularly when the homogenate is removed from the bag.

Regarding throughput, the FASTH device is capable of simultaneously processing 4 PRYPCON containers. While this system already provides a partly automated homogenization process, the alternative system using Stomacher bags is capable of processing only 2 bags at a time per device. The Bio-Rad system, in contrast, homogenizes 48 samples at a time.

However, during the sample preparation procedure of the Bio-Rad system, each grinding tube is closed manually with a screw cap. Twisting of the screw cap presses a seal onto the mouth of the container; the stronger the screw cap is twisted, the tighter the tube is sealed. That is to say, depending on the force exerted when twisting the cap to close the vial, the sealing effect of the screw cap may be imperfect. As a consequence of imperfect sealing, liquid contents of the vial may be released from a screw-capped vial, e.g., in case the pressure inside the vial rises relative to the outside due to a rise of temperature in the vial or a drop of air pressure outside. Thus, the use of screw caps poses a problem when "sealing" as a defined (i.e., standardized) state or result is to be obtained. An exemplary parameter for standardized sealing is air-tightness over a defined time interval against a measured relative difference of higher air pressure within the container and lower air pressure outside of the sealed container.

In addition, the use of screw caps requires increased manual handling by lab technicians and prevents rapid processing. Consequently, screw caps pose a problem when larger number of vials have to be opened and closed, or when it is desired to seal the vials automatically. In addition, the more manual handling is involved, the higher are the chances that vials with sample material are mistakenly interchanged.

The amount and the complexity of the material for single use which is needed to perform a TSE assay influence the price of an assay system. However, the amount of single use items and the material of which these are made particularly impact on the costs of waste disposal. Depending on national regulations, any waste material which has come in contact with infective TSE agent has to be subjected to chemical and/or heat treatment, autoclaving, or incineration. Due to the difficulties to inactivate infective prions, these processes are more cost-intensive compared to the inactivation of usual infective waste. Therefore, it is desired to minimize expenditure on waste disposal when running TSE tests at high throughput.

SUMMARY OF THE INVENTION

In view of the state of the art, the problem to be solved by the invention is to provide a prion test system which integrates all working steps including sample preparation, sample treatment and immunometric analysis in a single standardized format with a reduced burden of manual working steps. A further problem to be solved is to provide a prion test system which reduces the time until the final result of the test system is produced. At the same time it is desired that a high throughput test system for prion detection is robust and reliable, and that the workflow minimizes risks while potentially infectious material is processed. Also, a design of the test system is desired which minimizes the chances to mix up samples and/or test vials. Another problem to be solved is to provide a test system which economizes on components for single use and produces only a minimum amount of contaminated or potentially infective waste material.

According to the invention, the problem is solved by providing a method for performing a high throughput test to determine the presence of PrPsc in a tissue sample taken post mortem from brain, the test comprising the workflow of (A) sample preparation, (B) sample treatment, (C) sample analysis, (D) controls, and (E) classifying the results of the analysis as positive or negative, whereby (A) comprises the steps of (a) providing in a standardized format a rack with a set of individually labeled containers, whereby the container set comprises a subset for control reactions (control containers) to be processed as provided in (D) and a subset of containers for sample analysis (analysis containers); (b) providing within each analysis container (i) 3 to 6 spherical beads, whereby each bead weighs between 50 mg and 100 mg, and (ii) a volume of homogenization buffer, whereby the homogenization buffer contains a proteolytic enzyme capable of effecting proteolysis in the presence of a chaotropic agent; (d) providing a tissue sample from brain, whereby the tissue sample is identified by a label containing unique information defining the origin of the tissue sample; (e) performing the steps of (i) recording the label of the tissue sample, (ii) transferring the tissue sample into an analysis container, (iii) recording the label of the analysis container, (iv) correlating the recorded information of step (i) with the recorded information of step (iii), (v) repeating steps (i), (ii), (iii), and (iv) until the desired amount of analysis containers in the rack is filled with sample tissue; (f) performing the steps of (i) sealing the containers of the rack with sealing means, followed by (ii) agitating the rack with the containers using agitation means, whereby the agitation moves the beads from the bottom to the top of each analysis container, thereby homogenizing the sample tissue therein, followed by (iii) sedimenting tissue debris in the analysis containers, followed by (iv) opening the containers and aspirating out of each container an aliquot of supernatant; whereby (B) is to be performed after (A) and comprises the steps of (a) providing a microwell plate with each cavity containing as dry matter a predetermined amount of a chaotropic agent (conditioned microwell plate), whereby the chaotropic agent is attached to the wall of the cavity; followed by (b) transferring the supernatants of (A) step (f) into the cavities of the microwell plate, whereby the transferred volume is selected such that dissolving the dry matter in each cavity results in a concentration of between 300 mM and 2 M of the chaotropic agent in the supernatant; followed by (c) dissolving the chaotropic agent; followed by (d) incubating the microwell plate at a temperature between 15° C. and 50° C., thereby allowing proteolysis; followed by (e) inhibiting the activity of the proteolytic enzyme; followed by (f) increasing in the mixture in each well the concentration of the chaotropic agent to a value of between 3.5 M and 5 M; followed by (g) incubating the microwell plate under constant agitation at room temperature, whereby the components in the cavities are mixed, thereby providing treated samples; whereby (C) is to be performed after (B) and comprises the steps of (a) providing a microwell plate which is coated with streptavidin (detection microwell plate), (b) transferring an aliquot of each treated sample of (B) step (f) into a cavity of the detection microwell plate; followed by (c) adding to the aliquot a three- to ten-fold volume of detection solution containing a first and a second binding agent specific for two separate epitopes of unfolded PrP(27-30), whereby the first specific binding agent is biotinylated and the second specific binding agent is conjugated with a reporter enzyme; followed by (d) incubating the detection microwell plate under constant agitation thereby mixing the components in the cavities, and complexes of the specific binding agents and unfolded PrP(27-30) are allowed to form; followed by (e) removing the liquid from the cavities of the detection microwell plate and washing the cavities with washing buffer; followed by (f) adding reporter enzyme substrate solution to the cavities of the detection microwell plate and incubating the plate; followed by (g) performing the steps of (i) measuring in a cavity the turnover of the substrate as optical density (OD), thereby providing a measurement value for the cavity, followed by (ii) recording the measurement value, whereby an over-reading is recorded as OD=4.0, (iii) correlating the recorded measurement value of (ii) with the information recorded for the respective tissue sample in (A) step (e) step (i), (iv) repeating steps (i) to (iii) until the measurement values with regard to all tissue samples are processed, thereby providing analysis data relating to the samples; whereby (D) comprises the steps of (a) providing a reagent containing a recombinantly produced soluble fusion protein comprising the amino acid sequences of (i) one or more soluble carrier polypeptides, (ii) one or more epitopes of PrP(27-30) targeted by the first specific binding agent, and (iii) one or more epitopes of PrP(27-30) targeted by the second specific binding agent; (b) before performing the steps of (A) step (f) and the subsequent workflow, performing the steps of (i) recording the information of the labels of a first amount of control containers of (A) step (a), followed by (ii) providing in the first amount of control containers an aliquot of the homogenization buffer of (A) step (b) step (i), thereby providing negative controls, followed by (iii) correlating the recorded information of (i) with the negative controls, (iv) recording the information of the labels of a second amount of control containers of (A) step (a), followed by (v) providing in the second amount of control containers an aliquot of liquid selected from the group consisting of homogenization buffer lacking the proteolytic enzyme and homogenization buffer additionally containing an effective amount of a protease inhibitor, thereby providing positive controls, followed by (vi) correlating the recorded information of (iv) with the positive controls, followed by (vii) dispensing a measured amount of control reagent into each control container, (viii) including the positive and negative controls in (A) step (f), (B), and (C) steps (a) to (f); (c) performing the steps of (i) repeating (C) step (g) steps (i) to (iii) for each cavity of the detection microwell plate which contains a negative control until the measurement values with regard to all negative controls are processed, (ii) correlating the recorded measurement values of (i) with the information recorded for the negative controls, thereby providing negative control data, (iii) repeating (C) step (g) steps (i) to (iii) for each cavity of the detection microwell plate which contains a positive control until the measurement values with regard to all positive controls are processed, (iv) correlating the recorded measurement values of (iii) with the information recorded for the positive controls, thereby providing positive control data; whereby (E) is to be performed after (A), (B), (C), and (D), and comprises the steps of (a) calculating the median of the measurement values of the positive control data [M(p)] provided by (D) step (c); (b) calculating the median of the measurement values of the negative control data [M(n)] provided by (D) step (c); (c) calculating the median of the measurement values of the analysis data [M(a)] provided by (C) step (g); (d) calculating a cut-off value; (e) comparing the measurement value of a tissue sample provided by (C) step (g) with the cut-off value of (d); followed by (f) performing the steps of (i) classifying the measurement value as a positive test result if the measurement value is equal or greater than the cut-off value, or (ii) classifying the measurement value as a negative test result if the measurement value is smaller than the cut-off value, followed by (iii) recording the test result and correlating the test result with the information recorded for the respective tissue sample, followed by (iv) assigning the test result to the respective tissue sample; followed by (g) repeating steps (e) and (f) until the measurement values of all tissue samples are processed.

In addition, the invention provides a protein of the formula S-L1-S-L2-hPrP-His-tag, whereby S is the *E. coli* SlyD chaperone amino acid sequence SEQ ID NO: 1 or a fragment thereof, L1 and L2 are a first and a second glycine-rich linker amino acid sequence, hPrP is a fragment of the human prion preproprotein amino acid sequence according to SEQ ID NO: 3, and His-tag is a histidine tag sequence. The invention also provides a method for producing a protein according to the invention as well as use of the protein as well as a kit containing the same.

A further embodiment of the invention is a method for coating the wall of a cavity with a chaotropic agent, comprising the steps of (i) dissolving in water a first amount of the chaotropic agent and a second amount of a water-soluble helper substance; (ii) transferring an amount of the solution of step (i) into the cavity; and (iii) evaporating the solvent, thereby attaching a mixture of the chaotropic agent and the helper substance to the wall of the cavity. Yet a further embodiment of the invention is a conditioned microwell plate comprising a plurality of cavities, characterized in that the walls of one or more cavities are coated with a mixture of a water-soluble carbohydrate and a chaotropic agent. Yet a further embodiment of the invention is a conditioned microwell plate obtainable by the steps of: (i) providing a microwell plate; (ii) dissolving in water a first amount of the chaotropic agent and a second amount of a water-soluble helper substance; (iii) transferring an amount of the solution of step (ii) into one or more cavities of the microwell plate; and (iv) evaporating the solvent, thereby attaching a mixture of the chaotropic agent and the helper substance to the wall of the one or more cavities. Yet a further embodiment of the invention is the use of a conditioned microwell plate according to the invention for performing an assay for determining the presence or quantity of PrPsc in a biological sample. Yet a further embodiment of the invention is a kit of parts comprising a sealed bag made from a water-tight material and containing a conditioned microwell plate according to the invention.

Another embodiment of the invention is the use of a peptidic trypsin inhibitor to inhibit the proteolytic activity of Proteinase K. Yet another embodiment of the invention is a composition comprising water, Proteinase K, and a peptidic trypsin inhibitor. Yet another embodiment of the invention is a method to inhibit the proteolytic activity of Proteinase K in an aqueous composition, characterized in that a peptidic trypsin inhibitor is added to the composition at a concentration of between 50 and 150 times the molar concentration of Proteinase K. Yet another embodiment of the invention is a method for preparing a treated biological sample suspected of containing PrPsc such that it is suitable for specific detection of PrPsc, if present, the method comprising the steps of (a) homogenizing the sample; followed by (b) digesting the sample proteolytically by adding to the homogenate Proteinase K and incubating the sample; followed by (c) adding a peptidic protease inhibitor to the incubated mixture of step (b), thereby obtaining a treated biological sample suitable for specific detection of PrPsc, if present.

DETAILED DESCRIPTION OF THE INVENTION

Figure 1:
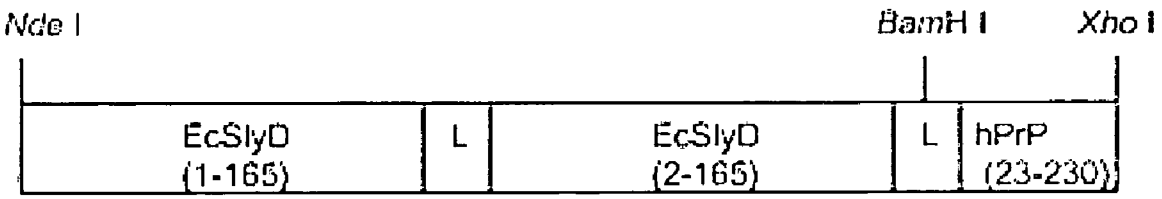
FIG. 1 Schematic diagram depicting the cassette according to Example 1 and SEQ ID NO: 5. EcSlyD(1-165) indicates a nucleotide sequence encoding the amino acid sequence of SEQ ID NO: 1 from position 1 to 165. EcSlyD(2-165) indicates a nucleotide sequence encoding the amino acid sequence of SEQ ID NO: 1 from position 2 to 165. L indicates a nucleotide sequence encoding the linker of SEQ ID NO: 2. hPrP(23-230) indicates a nucleotide sequence encoding a fragment of human prion preprotein given by the amino acid sequence of SEQ ID NO: 3 from position 23 to 230.

The invention is exemplified by an assay to detect BSE-infected cattle. However, the preferred monoclonal antibodies used in the assays of the invention are also reactive with prion protein species of hamster, mouse, sheep, and human. Alternatively, monoclonal antibodies specific for prion protein against one or more of the listed species are preferred. Therefore, the general method equally applies to other TSE assays. Alternatively, other antibodies capable of binding a TSE analyte can be provided, in order to perform an assay of the invention.

Certain terms are used with particular meaning, or are defined for the first time, in this description of the present invention. For the purposes of the present invention, the following terms are defined by their art-accepted definitions, when such exist, except that when those definitions conflict or partially conflict with the definitions set forth below. In the event of a conflict in definition, the meaning of the terms are first defined by the definitions set forth below.

The term "comprising" is used to mean "including, but not necessarily limited to". Further, it is understood that the term "about" in combination with a numerical value n indicates a value x in the interval given by the numerical value ±5% of the value, i.e., $n-0.05*n \leqq x \leqq n+0.05*n$. In case the term "about" in combination with a numerical value n describes a preferred embodiment of the invention, the value of n is most preferred, if not indicated otherwise.

If not indicated otherwise the use of the indefinite article "a"/"an" in combination with a noun which terms an item, e.g., "a microplate", "a protein", "an antibody", is understood as having the meaning of "at least one".

The term "microwell plate" denotes a plastic sample holder widely used in biology, biochemistry and chemistry. For microwell plates a standard was formalized by the Society for Biomolecular Screening (SBS) in 1996. A microwell plate typically has 96, 384 or even 1536 sample wells (also referred to as cavities) arranged in a 2:3 rectangular matrix. The standard governs cavity dimensions (e.g., diameter, spacing and depth) as well as plate properties (e.g., dimensions and rigidity). Also known to the art are racks with containers such as tubes which have identical dimensions as microwell plates regarding base surface area, and the spacing of the tubes correlates with the spacing of microwell plate cavities. A number of companies have developed automatic handling devices ("robots") to specifically handle SBS microwell plates as well as other items having dimensions compatible with the SBS standard. By these means human work, such as in the manipulation of hazardous materials is either replaced or enhanced. These robots may be liquid handlers which aspirate or dispense liquid samples from and to these plates, for example by multi-channel pipetting means, or "plate movers" which transport them between instruments. Instrument companies also have designed plate readers. Plate readers are laboratory instruments designed to detect biological, chemical or physical events in samples stored in microwell plates.

The term "aliquot" denotes a subsample derived by a divisor that divides a sample or, more generally, a larger whole into a number of equal parts; thus, an aliquot is a subsample or representative portion of the sample resulting from such a division. If not indicated otherwise it is understood that aliquots of samples which are transferred from either an array of containers or a first microwell plate to a second microwell plate are equal amounts. For example, when an aliquots of liquid samples stored in the cavities of a first microwell plate are transferred to the cavities of a second microwell plate by way of pipetting, each single transfer transmits an equal volume.

"PrP" denotes the prion protein. It can exist in various forms. One is known as PrPc and is the normal, non-disease type of the protein that is found on the surface of particular cell types. One is known as PrPsc that is found in the brains of individuals infected with TSE. PrPsc is also known as PrPres, indicating that it is difficult to break down with proteinases. PrP(27-30) is a fragment of the prion protein which has been broken up proteolytically by Proteinase K.

The term "chaperone" denotes a protein that assists the correct folding of proteins in vivo; chaperones do not themselves form part of the structures they help to assemble.

Amino acid identification uses the three-letter abbreviations as well as the single-letter alphabet of amino acids, i.e., Asp D Aspartic acid, Ile I Isoleucine, Thr T Threonine, Leu L Leucine, Ser S Serine, Tyr Y Tyrosine, Glu E Glutamic acid, Phe F Phenylalanine, Pro P Proline, His H Histidine, Gly G Glycine, Lys K Lysine, Ala A Alanine, Arg R Arginine, Cys C Cysteine, Trp W Tryptophan, Val V Valine, Gln Q Glutamine, Met M Methionine, Asn N Asparagine. An amino acid at a particular position in an amino acid sequence is given by its three-letter abbreviation and a number. As an example, referring to the amino acid sequence of SEQ ID NO: 3, "Pro60" denotes the Proline residue at amino acid position 60.

The term "Optical density" or "OD" denotes the ability of a material to absorb light. The darker the material, the higher the optical density. Optical density is usually expressed on a logarithmic scale of Optical Density (OD) units.

The design of a high throughput prion detection assay demands simplicity and effectiveness. Generally, reducing the number of manual steps in the workflow of the assay is advantageous. To this end, a high throughput requires that every single step in the workflow is made in a highly standardized fashion. For example, a pipetting step needs to be designed in order to ensure the transfer of a measured amount of liquid which has to be within accepted error margins. The same applies to the incubation time when the homogenized sample material is treated with Proteinase K. Also, mechanical actions like opening or closing/sealing a container or a vial are advantageously designed such that after the working step the container is either open or closed and that no imperfect or intermediate states (e.g., closed but not sealed, that is air/water tight) are possible. To this end, standardizing a working step within the workflow is understood to be the improvement of the working step in order to result in an outcome with an error margin, whereby any result tolerated by the error margin still supports all subsequent working steps, provided that the outcome of each subsequent working step is within each respective error margin.

The workflow of the assay according to the invention for the detection of prions in samples of bovine brain stem comprises (A) sample preparation, (B) sample treatment, (C) sample analysis, (D) controls, and (E) classifying the results of the analysis as positive or negative. Preferably, the number of tissue samples with expected negative test results is higher than the number of tissue samples with expected positive test results.

(A) Sample Preparation

The inventors have devised a way which allows the use of containers in racks of a standardized format, not only for sample treatment and analysis but also for the preceding steps of sample preparation. According to the invention, sample preparation (A) comprises the steps of (a) providing in a standardized format a rack with a set of individually labeled containers, whereby the container set comprises a subset for control reactions (control containers) to be processed as provided in (D) and a subset of containers for sample analysis (analysis containers); (b) providing within each analysis container (i) 3 to 6 spherical beads, whereby each bead weighs between 50 mg and 100 mg, and (ii) a volume of homogenization buffer, whereby the homogenization buffer contains a proteolytic enzyme capable of effecting proteolysis in the presence of a chaotropic agent; (d) providing a tissue sample from brain, whereby the tissue sample is identified by a label containing unique information defining the origin of the tissue sample; (e) performing the steps of (i) recording the label of the tissue sample, (ii) transferring the tissue sample into an analysis container, (iii) recording the label of the analysis container, (iv) correlating the recorded information of step (i) with the recorded information of step (iii), (v) repeating steps (i), (ii), (iii), and (iv) until the desired amount of analysis containers in the rack is filled with sample tissue; (f) performing the steps of (i) sealing the containers of the rack with sealing means, followed by (ii) agitating the rack with the containers using agitation means, whereby the agitation moves the beads from the bottom to the top of each analysis container, thereby homogenizing the sample tissue therein, followed by (iii) sedimenting, preferably by centrifugation, tissue debris in the analysis containers, followed by (iv) opening the containers and aspirating out of each container an aliquot of supernatant.

It is preferred that the tissue sample is taken post mortem. Preferred samples are lymph node, tonsil and brain tissue. In case the sample is taken from lymph node or tonsil tissue, the tissue can also be sampled from living individuals. However, a brain tissue sample taken post mortem is most preferred. Also preferred, the tissue sample has a weight of between 100 mg and 200 mg, more preferred between 125 mg and 175 mg. Even more preferred, the sample has a weight of about 150 mg, most preferred 150 mg±30 mg. Preferably, the tissue sample is taken from the brain stem of cattle, sheep, elk or deer. Also, a human tissue sample taken post mortem is preferred. More preferred, the tissue sample is taken from obex material. Even more preferred, the sample material is removed from the obex using tissue cutting means. Most preferred is the use of a tissue cutter which is capable of punching out a piece of tissue of defined mass. Also preferred, the tissue sample is an autolysed brain tissue sample. In the latter case a defined amount of sample is taken e.g., by pipetting.

The tissue sample is then transferred into a sample container, also referred to as a "container". The container is a single vial in a rack with standardized dimensions. Preferably, the standardized format of the rack is a 8×12 format and the rack contains a set of 96 containers. A subset of at least 16 containers per set are preferably used for control reactions. Thus, of a set of 96 containers at least 8 and up to 80 containers are preferably used as analysis containers.

Preferably, the width of the opening of a single container is similar to the width of the opening of a single cavity in a standard 8×12 format (also referred to as "96-well") microwell plate. The term "similar width" indicates that the round opening of a single container differs from the width of the opening of a single cavity in a standard 96-well microwell plate by not more than 10%. All containers in the rack are preferably identical with regard to shape, size and volume. The positions of the containers in the rack are the same as the positions of the cavities in a standard 96-well microwell plate. This arrangement advantageously allows the use of multi channel pipetting means for standard format microwell plates when transferring amounts of liquid into the containers.

It is preferred that each container has a substantially cylindrical shape, with a circular mouth at the top. The bottom of the container may be a flat bottom or, preferred, a U-shaped bottom. Preferably, the container has a volume of between 1 ml and 2 ml, more preferred between about 1.3 ml to about 1.6 ml, most preferred about 1.4 ml. Even more preferred, the container has a diameter of about 9 mm. Suitable containers and racks to practice the invention are exemplified by the product with the trade name Traxis polypropylene rack with cover, filled with Traxis 1.4 ml polypropylene 2D coded tubes provided by Micronic BV (Lelystad, The Netherlands) which are distributed by Integra Biosciences. The rack with the containers come in the 8×12 format. However, other containers and racks are possible.

The use of the 8×12 format for the entire procedure is advantageous over the state of the art. Particularly, when preparing containers for sample preparation as parts of a high throughput prion assay kit, use of the 8×12 format makes pre-filling of the containers with a homogenization buffer unnecessary as this can be done more efficiently using multi-channel pipetting devices and, very much preferred, by means of a pipetting robot. As a consequence, the containers do not need to be sealed individually and no buffer can leak from improperly closed containers during transport or storage. In addition, the ingredients for preparing the homogenization buffer can be provided as dry material for reconstitution of the buffer. Dry materials allow for a longer shelf life of a kit for tissue homogenization. Dispensing of reconstituted homogenization buffer can be done effectively using multi channel pipetting means, preferably automated.

Before the sample tissue is transferred into an analysis container the analysis container is loaded with a defined amount of spherical beads. Preferably, 2 to 6 beads, most preferred 4 beads are loaded into each container. It is preferred that each bead weighs between 50 mg and 100 mg. More preferred, the beads consist of a material or a mixture of materials with a specific weight of at least 5 $g/cm^3$ and up to 8 $g/cm^3$. Most preferred, the specific weight is about 6 $g/cm^3$. Preferred beads are characterized by a low wear of friction during the homogenization process. It is also preferred that the surface of the beads consists of a material which has a low binding affinity to PrPsc. More preferred, the material is a material other than metal. Even more preferred, the surface of the beads consists of Zirconia. Even more preferred, the beads entirely consist of Zirconia. Zirconia is a white crystalline oxide; it is known to the art from its use as cell disruption means. It is very much preferred that the beads are of similar size. Importantly, the size of the beads is selected such that the inner diameter of the cylindrical container exceeds the diameter of any bead by at least about 3 mm. Most preferred, each single bead has a diameter of about 3 mm±0.2 mm and a weight of about 80 mg, that is to say between 75 mg and 85 mg. Exemplary beads to practice the invention are commercially available from Retsch GmbH & Co. KG (Haan, Germany), article no. 05.368.0090.

Also very much preferred, the beads are dispensed into the containers using a bead dispensing device. These devices are commercially available, e.g., from Qiagen GmbH, Hilden, Germany (catalogue number 69973 or 69975). With great advantage, before performing sample preparation racks holding containers loaded with beads are covered by lids. Most preferred, a lid, when covering the rack, prevents the beads from falling out of the containers in case a rack is tilted. Thereby racks with containers pre-loaded with beads can be provided ahead of the sample preparation procedure and stored, whereby the handling of racks is facilitated.

Each container carries a unique label which allows to unambiguously identify the container within a single rack. Also preferred, each rack carries a unique label. It is more preferred that each container carries a unique label which allows to unambiguously identify the container within a plurality of racks. Thus, when a tissue sample is transferred to a container the tissue sample is assigned to the unique label of the container which can be tracked further on. In this regard it is very much preferred that the label on each container is designed such that it can be read by automated means. An example therefor is a one-dimensional or two-dimensional bar code. Preferably, the label is positioned on the bottom of the container. In practice, the label issued by the veterinarian at the abattoir, which identifies the animal from which the tissue sample origins, is read out, preferably by automated means. Subsequently, the label of the container in which the tissue sample is stored is read out. The information of the two labels is stored as data sets in a database, and a link between the two data sets is established. The storage of information, the assignment of a sample to its container and its further tracing (tracking) is preferably controlled by a computer. The computer also provides storage means for tracking data as well as analysis software for analyzing tracking data.

Before the tissue samples are stored in the analysis containers, a measured volume of homogenization buffer is transferred to each analysis container. Preferably, between 500 μl and 1 ml of homogenization buffer is provided within each container. More preferred, a volume of 900 μl of homogenization buffer is provided.

Generally, pipetting such as transferring of the homogenization buffer are performed by pipetting means, either for manual or automated operation. Very much preferred pipetting means is a multi-channel pipetting device. There are several multi-channel pipetting devices known to the skilled person. Examples are pipettes with 8 or 12 channels to be operated by hand. Very much preferred, the multi-channel pipette is operated by an automated device such as a pipetting robot. Even more preferred, the multi-channel pipette is selected from the group consisting of a multi-channel pipette with 8 channels, a multi-channel pipette with 12 channels, a multi-channel pipette with 48 channels, and a multi-channel pipette with 96 channels.

It is preferred that the homogenization buffer is an aqueous buffer with a pH between 7 and 8 which comprises a detergent, an uncharged water-soluble sugar, a buffer salt, and a complexing agent capable of complexing bivalent cations. It is more preferred that the homogenization buffer comprises sodium lauryl sarcosine, Saccharose, HEPES, and EDTA. It is also preferred that the homogenization buffer contains Proteinase K (e.g., recombinantly produced Proteinase K; Roche Diagnostics GmbH, Mannheim, Germany, e.g., catalogue number 3115852). Most preferred, the homogenization buffer does not contain a chaotropic agent such as urea, sodium iodide or a guanidinium salt.

As the homogenization buffer contains Proteinase K, starting the homogenization process by agitation later on triggers proteolytic digestion, however within limits as far as PrPsc is concerned. It was found that before the onset of agitation any digestion processes have little if any impact on the outcome of the assay.

The activity of the Proteinase K regarding this target is enhanced by the addition of a chaotropic agent in a later working step. The chaotropic agent then multiplies the effect of Proteinase K by partially denaturing PrPsc while leaving the proteolytic activity of the enzyme largely unaffected.

After adding the homogenization buffer, the containers in the rack are sealed using stopper caps. Most preferred is the use of stopper caps provided as a sealing mat as described in WO 01/017682. Stopper caps for single use are very much preferred. Also very much preferred, the stopper caps consist of a flexible material. The preferred sealing mat-is in the 8×12 format and holds 96 stopper caps. The positions of the caps are aligned with the positions of the openings of the containers in the rack. The mat is placed onto the rack such that the bottom end of each stopper is located above the opening of a container. The bottom portions of the stopper caps are then pressed into the mouths of the containers by applying pressure on the mat. This can be done using a roller. Subsequently, the mat is removed from the rack whereby the stopper caps remain in the containers. It is preferred to use a "Capcluster" mat together with a "capmat sealer" device which are provided by Micronic BV (Lelystad, The Netherlands). As the sealing process is amenable to automation, sealing the containers using an automated device is very much preferred.

The rack with the sealed containers is then placed into the holder of an agitating device. Preferably, the holder is in principle designed like a vice and holds the rack by pressing against the bottom of the rack and the stopper caps sealing the containers.

The tightness of sealing can be adjusted, that is increased if necessary, by increasing the pressure of the holder against the stopper caps. The skilled person will determine the tightness of the sealing, e.g., by filling the containers halfway with water or another liquid, closing and sealing the containers, inverting the rack holder or casing so that the liquid phase in the containers completely covers the stopper caps, reducing the ambient air pressure by a measured amount and determining whether any liquid phase leaks out from the containers.

The rack with the sealed containers is agitated by agitating means, that is a means to apply oscillating movement. Preferably, the agitation means is a shaking device. A very much preferred shaking device is the TissueLyzer Mixer Mill MM 300 which is distributed by Qiagen GmbH, Hilden, Germany. The Mixer Mill MM 300 provides a rack holder which comprises contact jaws to fix the rack and at the same time applies pressure on the stopper caps.

In each container the agitation causes the beads to move from the bottom of the container to the top, thereby homogenizing the sample tissue. Preferably, the casing is positioned such that the containers are oriented horizontally while being agitated. It is preferred that the containers are agitated with a frequency of more than 10 Hz and up to 100 Hz. Very much preferred is a frequency of about 30 Hz. The frequency of 30 Hz corresponds to the maximum speed of the Mixer Mill MM 300.

In order to ensure that the oscillating movement applied by the agitating device is applied to all containers in a similar fashion and is independent of the geometry of the movement, the movement is applied in two passes. After the first pass the rack with the containers is turned by 180° and the second pass is applied. It is preferred that in each pass the sample is agitated at least 30 sec and not more than 15 min. More preferred, in each pass the sample is agitated for about 5 min.

Subsequently, the rack with the containers is removed from the agitating device. Tissue debris is then sedimented. Preferably, the tissue debris is sedimented by centrifuging the rack, more preferred by centrifuging for 2 min at 1,000×g. All homogenization steps including the centrifugation step are preferably performed at a temperature between 15° C. and 30° C., most preferred at 22° C.±5° C.

Following centrifugation of the rack the stopper caps are removed from the containers using a cap removal tool ("decapper", distributed by Micronics BV); the stopper caps are discarded. Removal of the sealing means is amenable to automation which is very much preferred. Out of each container a volume 150 μl of the supernatant (that is the homogenate without larger chunks of debris) is pipetted into the corresponding cavity of the "digestion/unfolding plate". This step can be performed automatically. Preferably, the pipetting is done using a multi channel pipetting device. Afterwards, the containers with the residual homogenates are sealed again using disposable stopper caps as described above and stored. Preferably, the containers are stored for up to 8 h at 5° C.±3° C. Also preferred, the containers are stored for up to 1 month at −20° C.±5° C.

It is very much preferred to use automated sample tracking. Therefore, in the most preferred method of the invention (A) additionally comprises providing a computer equipped with reading means, a database, database management software, sample tracking software, and data output means; and (A) step (e) comprises performing the steps of (i) reading the label of the tissue sample into the computer and storing the information of the label into the database, (ii) transferring the tissue sample into an analysis container, (iii) reading the label of the analysis container into the computer and storing the information of the label into the database, (iv) correlating the stored information of step (i) with the stored information of step (iii), (v) repeating steps (i), (ii), (iii), and (iv) until the desired amount of analysis containers in the rack is filled with sample tissue.

(B) Sample Treatment

According to the invention, (B) is to be performed after (A) and comprises the steps of (a) providing a microwell plate with each cavity containing as dry matter a predetermined amount of a chaotropic agent (conditioned microwell plate), whereby the chaotropic agent is attached to the wall of the cavity; followed by (b) transferring the supernatants of (A) step (f) into the cavities of the microwell plate, whereby the transferred volume is selected such that dissolving the dry matter in each cavity results in a concentration of between 300 mM and 2 M of the chaotropic agent in the supernatant; followed by (c) incubating the microwell plate, preferably under constant agitation at room temperature, thereby dissolving the chaotropic agent; followed by (d) incubating the microwell plate, preferably under constant agitation, at a temperature between 15° C. and 50° C., preferably between 35° C. and 45° C., most preferred at 42° C., thereby allowing proteolysis; followed by (e) inhibiting the activity of the proteolytic enzyme, e.g., by adding to the mixture in each well an effective amount of a protease inhibitor; (f) increasing in the mixture in each well the concentration of the chaotropic agent to a value of between 3.5 M and 5 M; followed by (g) incubating the microwell plate under constant agitation at room temperature, whereby the components in the cavities are mixed, thereby providing treated samples.

The "digestion/unfolding plate" is a "conditioned" microwell plate. During the digestion/unfolding step the homogenate is treated with a proteolytic enzyme, preferably Proteinase K, in the presence of a chaotropic agent. Under the conditions according to the invention the proteolytic enzyme hydrolyzes PrPc. However, a fragment of PrPsc resists the protease and remains available for the detection. The protease-resistant PrPsc fragment is also referred to as "PrP(27-30)". Very much preferred, the homogenate is digested with Proteinase K at between 2 μg/ml to 2 mg/ml. Most preferred is a concentration of about 100 μg/ml. Also most preferred, the homogenate is digested in the presence of about 1 M guanidine hydrochloride.

The chaotropic agent is provided on the conditioned plate as dry material. The conditioning process is described further below. Preferably an absolute amount of between 50 μM and 300 μM of the dry chaotropic agent is provided in each cavity of the conditioned microwell plate. More preferred is an absolute amount of between 100 μM and 200 μM of the dry chaotropic agent. Most preferred is an amount of 150 μM of the dry chaotropic agent.

When the supernatants are transferred, the coordinates of each sample on the 8×12 digestion/unfolding plate are preferably kept identical as in the 8×12 container rack. Cavities of a microplate containing samples which can be traced back to analysis containers are also referred to as analysis cavities; likewise, cavities which can be traced back to control containers are also referred to as control cavities. The digestion/unfolding plate is preferably labeled. It is very much preferred that the label of the plate is recorded and the recorded information of the plate label is correlated with the recorded information of the rack holding the containers from which the supernatant is transferred into the cavities of the plate. More preferred, when using automated sample tracking, the label of the plate is read into the computer and the information of the label is stored into the database. The stored information of the plate label is correlated with the stored information of the rack holding the containers from which the supernatant is transferred into the cavities of the plate.

In order to provide the means for an even higher throughput of samples and controls, the present invention contemplates performing the digestion/unfolding step as well as all subsequent steps in microwell plates in the format with 384 cavities (also referred to as "384-format"). Apart from adaptations necessary with regard to volumes to be transferred to 384-format microplates, mixing of liquids by way of agitation may produce suboptimal results. In such a case alternative mixing means have to be applied, such as applying ultrasound, temperature-induced convection or vibrating needles. Alternatively, ceramic beads, preferably zirconia beads, can be added into the wells so that upon agitation of the microwell plate movement of the beads supports mixing. In addition, when using microwell plates in the 384-format, sample tracking is routinely adopted by assigning a sample which in the beginning is homogenized in a container in a rack of the 9*12 format to a cavity on a coordinate of a microplate in the 384-format. Preferably, for the sample the coordinate on the digestion/unfolding microplate in the 384-format is maintained during subsequent steps, that is on the detection microplate in the 384-format. However, in the subsequent text, the description only takes into account the use of 8×12 microwell plates.

Upon adding the supernatants the digestion/unfolding plate is sealed with sealing film and placed on a running shaker. The plate is preferably incubated with constant agitation at 700 r.p.m.±50 r.p.m. (rounds per min). A first incubation is performed for 14 min±2 min at 22° C.±5° C. under constant humidity. The microplate is then placed on a running shaker in a temperature chamber at 42° C.±2° C. and incubated with constant agitation at 700 r.p.m.±50 r.p.m. (rounds per min) 30 min±2 min under constant humidity.

The invention additionally encompasses a method for preparing a treated biological sample suspected of containing PrPsc such that it is suitable for specific detection of PrPsc, if present, the method comprising the steps of (a) homogenizing the sample; followed by (b) digesting the sample proteolytically by adding to the homogenate Proteinase K and incubating the sample; followed by (c) adding a peptidic protease inhibitor to the incubated mixture of step (b), thereby obtaining a treated biological sample suitable for specific detection of PrPsc, if present. A peptidic protease inhibitor is a peptide capable of forming a complex or a conjugate with Proteinase K, thereby irreversibly inhibiting the proteolytic activity of Proteinase K. A preferred peptidic protease inhibitor for the purpose of the invention is a trypsin inhibitor. A preferred trypsin inhibitor is a trypsin inhibitor from soybean. More preferred is a trypsin inhibitor from egg white. A most preferred trypsin inhibitor from egg white is available from Roche Diagnostics GmbH (Mannheim, Germany, catalogue number 0109878). In order to ensure effective inhibition of Protease K, the concentration of the trypsin inhibitor is between 50 and 150 times, preferred 100 times, the molar concentration of Proteinase K in the mixture of step (b). Thus, the invention also encompasses a composition containing Proteinase K and a trypsin inhibitor. Preferably, the composition additionally contains a chaotropic agent. More preferred, the composition additionally contains a detergent. Even more preferred, the composition additionally contains material of a biological sample suspected of containing PrPsc. Most preferred, the material of the biological sample is homogenized, lysed or has undergone autolysis.

The digestion of (B) step (d) is ended by adding an effective amount of a peptidic protease inhibitor and increasing the concentration of guanidine hydrochloride, preferably to a concentration between 3.5 M and 4 M (including 3.5 M and 4 M).

A most preferred protease inhibitor is a trypsine inhibitor from soybean. Also preferred is adding trypsin inhibitor to a final concentration of between 10 mg/ml and 20 mg/ml, even more preferred to a final concentration of between 12 mg/ml and 15 mg/ml. Preferably, the trypsine inhibitor and the additional guanidine hydrochloride are added together as a concentrated solution, which is also referred to as "unfolding reagent". The increased concentration of the chaotropic agent causes the Proteinase K-resistant PrP(27-30) to unfold. Unfolded PrP(27-30) as an antigen is similar to the corresponding portion of PrPc. Particularly, certain antibodies specific for PrPc can be used to detect unfolded PrP(27-30).

The trypsine inhibitor in the unfolding reagent is needed to inhibit the proteolytic activity of Proteinase K during the present and subsequent steps. Following the addition of the unfolding reagent an incubation is performed, preferably with constant agitation at 400 r.p.m.±50 r.p.m.; the incubation time after adding the unfolding reagent is preferably between 15 min and 30 min, most preferred 20 min±2 min. The incubation temperature is preferably 22° C.±5° C.

The amount of chaotropic salt which has to be added to the homogenate upon transfer to the digestion/unfolding plate could, in principle, also be added by mixing a concentrated solution with the homogenate, whereby the volume of the sample solution increases. As the unfolding reagent has to be added as a concentrated solution the problem arises that the higher the volume of the sample solution, the higher the needed concentration of the unfolding reagent. However, the volume of any solution advantageously should be as small as possible since the digestion/unfolding steps are to be performed in the limited space of a microwell cavity. Also, the viscosity of the concentrated solutions and the sample solution may pose a problem. A highly viscous concentrated solution can make dispensing of the solution by means of pipetting devices difficult and inaccurate.

This problem is at least in part overcome by the invention which provides a "conditioned" digestion/unfolding plate. Thus, according to the invention there is provided a method for conditioning cavities of a microwell plate, comprising the steps of dispensing a solution of guanidine hydrochloride dissolved in water into the cavities of the microwell plate, followed by evaporating the water. The method of the invention is a preferred method of providing dry guanidine hydrochloride in the analysis cavities. According to the invention it is preferred to attach the guanidine hydrochloride to the walls of the cavities using a water-soluble helper substance. The helper substance is selected by its ability to include the chaotropic salt and completely stick to the wall of the cavity when the solvent is evaporated. Thus, the invention provides a conditioned microplate comprising a plurality of cavities, characterized in that the walls of one or more cavities are coated with a mixture of a water-soluble helper substance and a chaotropic agent. The invention also provides a method for conditioning cavities of a microwell plate by attaching to the walls of the cavities a chaotropic substance, comprising the steps of dissolving in water a first amount of the chaotropic substance and a second amount of a water-soluble helper substance, followed by transferring an amount of the solution into the cavities of the microplate, followed by evaporating the solvent, thereby attaching the mixture of the chaotropic agent and the helper substance to the wall of the cavity. The invention thus provides a conditioned microwell plate, obtainable by performing the steps of (i) providing a microwell plate; (ii) dissolving in water a first measured amount of a chaotropic agent and a second measured amount of a water-soluble carbohydrate, thereby forming a conditioning solution; followed by (iii) dispensing a measured volume of the conditioning solution into one or more cavities of the microwell plate; followed by (iv) evaporating the solvent, thereby attaching the chaotropic agent and the carbohydrate to the walls of the cavities, thereby obtaining a conditioned microplate.

It is preferred that the chaotropic substance is selected from the group consisting of urea, a guanidinium salt, and mixtures thereof. More preferred, the chaotropic substance is a guanidinium salt. Even more preferred is a guanidinium salt selected from the group consisting of guanidinium thiocyanate, guanidinium isothiocyanate, guanidinium hydrochloride, or mixtures thereof. Guanidinium hydrochloride is most preferred. A preferred helper substance is a carbohydrate. It is more preferred that the helper substance is selected from the group consisting of a sugar monomer, a sugar oligomer, and a sugar polymer. Even more preferred, the water-soluble carbohydrate is selected from the group consisting of a monosaccharide, a disaccharide, and a trisaccharide.

The helper substance should not interfere with the detection of unfolded PrP(27-30) in subsequent steps. Thus, when selecting a helper substance the skilled person has to compare the performance of the assay with and without the helper substance under consideration. A most preferred helper substance is saccharose. The concentration of the helper substance is preferably between 10 mM and 500 mM, more preferred between 50 mM and 100 mM. Most preferred is conditioning the cavities of the microwell plate with an aqueous solution containing 3 M guanidine hydrochloride and 20 mg/ml saccarose. Most preferred, a volume of 50 μl of the solution is transferred into each analysis cavity of a 8×12 microplate and subsequently the water is evaporated from the microwell plate.

Upon drying, the remaining water in the mixture of the chaotropic agent and the helper substance is preferably between 0.5% and 5% (weight by weight) of the dried mixture., preferred about 1%. The inventors noted that the helper substance also reduces the effect of the hygroscopic chaotropic substance taking up water from the humidity in the ambient atmosphere. Nevertheless, storing a conditioned microwell plate in an air- and water-tight bag such as a sealed plastic bag in the presence of drying material such as silica gel is preferred.

As outlined herein, the invention also provides the use of a conditioned microplate according to any of the claims 7 to 10 for performing an assay. Preferably, the assay determines the presence or quantity of PrPsc in a biological sample. The invention also contemplates a kit of parts comprising a sealed bag made from a water-tight material and containing a conditioned microplate according to the invention. Preferably, the kit additionally comprises drying material present in the bag containing the conditioned microplate.

(C) Sample Analysis

The subsequent working steps are directed to the detection of the analyte, i.e., unfolded PrP(27-30) in the treated sample solution. According to the invention, (C) is to be performed after (B) and comprises the steps of (a) providing a microwell plate which is coated with streptavidin (detection microwell plate), (b) transferring an aliquot of each treated sample of (B) step (f) into a cavity of the detection microwell plate; followed by (c) adding to the aliquot a three- to ten-fold volume of detection solution containing a first and a second binding agent specific for two separate epitopes of unfolded PrP(27-30), whereby the first specific binding agent is biotinylated and the second specific binding agent is conjugated with a reporter enzyme; followed by (d) incubating the detection microwell plate under constant agitation thereby mixing the components in the cavities, and complexes of the specific binding agents and unfolded PrP(27-30) are allowed to form; followed by (e) removing the liquid from the cavities of the detection microwell plate and washing the cavities with washing buffer; followed by (f) adding reporter enzyme substrate solution to the cavities of the detection microwell plate and incubating the plate; followed by (g) performing the steps of (i) measuring in a cavity the turnover of the substrate as optical density (OD), thereby providing a measurement value for the cavity, followed by (ii) recording the measurement value, whereby an over-reading is recorded as OD=4.0, (iii) correlating the recorded measurement value of (ii) with the information recorded for the respective tissue sample in (A) step (e) step (i), (iv) repeating steps (i) to (iii) until the measurement values with regard to all tissue samples are processed, thereby providing analysis data relating to the samples.

In order to facilitate automatic sample tracking, (C) step (g) of the workflow preferably comprises performing the steps of (i) measuring in a cavity the turnover of the substrate as optical density (OD), thereby providing a measurement value for the cavity, followed by (ii) reading the measurement value into the computer of (A) step (b), whereby an over-reading is set as OD=4.0, (iii) storing the measurement value in the database, (iv) correlating the stored measurement value of (ii) with the information stored for the respective tissue sample, (v) repeating steps (i) to (iv) until the measurement values with regard to all tissue samples are processed, thereby providing analysis data relating to the samples.

A preferred specific binding agent is, e.g., a receptor for unfolded PrP(27-30), more preferred an antibody to unfolded PrP(27-30). A specific binding agent has at least an affinity of $10^7$ l/mol for its corresponding target molecule. The specific binding agent preferably has an affinity of $10^8$ l/mol or even more preferred of $10^9$ l/mol for its target molecule. As the skilled person will appreciate the term specific is used to indicate that other biomolecules present in the sample do not significantly bind to the binding agent specific for unfolded PrP(27-30). Preferably, the level of binding to a biomolecule other than the target molecule results in a binding affinity which is only 10%, more preferably only 5% of the affinity of the target molecule or less. A most preferred specific binding agent will fulfill both the above minimum criteria for affinity as well as for specificity. A specific binding agent preferably is an antibody reactive with unfolded PrP(27-30). The term antibody refers to a polyclonal antibody, a monoclonal antibody, fragments of such antibodies, as well as to genetic constructs comprising the binding domain of an antibody.

Very much preferred monoclonal antibodies for binding of the analyte are obtained as described in WO 00/26238. The monoclonal antibodies of a preferred antibody pair, i.e., a first (capture) and a second (detection) antibody specifically recognize prion protein in its cellular form (PrPc). More preferred, they also recognize unfolded linearized forms of PrPc and PrPsc including the Proteinase K truncated 27-30 kD form of PrPsc [i.e., PrP(27-30)]. Even more preferred, the antibodies of the assay according to the invention react independently of glycosylation of PrPc. Even more preferred, the antibodies are specific for the beta-form of PrP. Therefore, binding of the antibodies to PrPsc requires an unfolding step. Thus, most preferred antibodies are capable of binding to PrP(27-30) under conditions which support the presence of unfolded PrP(27-30). Preferably, unfolded PrP(27-30) is bound by a first and a second specific monoclonal antibody, whereby the first antibody is biotinylated and the second antibody is conjugated with a reporter enzyme such as alkaline phosphatase or peroxidase. Peroxidase (POD) is most preferred.

Following the unfolding step, a volume of preferably 30 μl to 50 μl, most preferred 40 μl, of the sample solution is transferred from each cavity of the digestion/unfolding plate to the corresponding cavity of a detection plate. That is to say, the coordinates of the cavities on the digestion/unfolding plate and the detection plate are identical for any given sample solution. The detection plate is coated with streptavidin. More preferred, the detection microwell plate is coated with heat-treated bovine serum albumin coupled with streptavidin as described in EP 0 269 092. It was noted by the inventors that the high guanidine concentration of about 4 M does not have an adverse effect on the coating of the detection plate. Subsequently, an about five-fold volume, most preferred 200 μl, of a detection solution containing a first biotin-conjugated capture antibody and a second POD-conjugated detection antibody is added and mixed. Preferably, the volume of the detection solution is chosen to effectively reduce the concentration of guanidine to a concentration in the range of between 0.1 M to 1 M, preferably in the range of between 0.3 M to 0.8 M, more preferred in the range of between 0.5 to 0.7 M, even more preferred to a concentration of about 0.65 M. The plate is sealed with sealing film and the mixture is incubated, preferably on a shaker at 400 r.p.m.±50 r.p.m. for 60 min±5 min at 22° C.±5° C.

When developing the assay it was found that the complex of unfolded PrP(27-30) and the first and the second antibody forms in the presence of guanidinium hydrochloride at a concentration of about 0.65 M. At the same time, under these conditions the complex binds to the streptavidin-coated walls of the microwell plate. Moreover, the conjugated peroxidase enzyme remains active. Thus, detection of unfolded PrP(27-30) according to the invention is possible as a one-step procedure.

After the incubation the cavities of the microwell plate are washed three times with a washing solution. Thereafter, the cavities are filled with a volume of TMB substrate solution, preferably 200 μl. The plate is incubated, preferably on a shaker at 400 r.p.m.±50 r.p.m. for 10 min±2 min at 22° C.±5° C. The incubation is stopped by adding a volume of TMB stop solution, preferably 200 μl. The plate is placed into a microwell plate reader, preferably within 10 min. The absorbance at a wavelength of 450 nm is measured and the absorbance at 620 nm is subtracted. The resulting value is recorded as the measurement value for the optical density (OD). Sometimes an "over-reading" may be observed. An over-reading is obtained when the optical density of the solution in a cavity exceeds the upper limit of detection of the microwell plate reader. In such a case the OD value is arbitrarily set as 4.0, in order to allow the calculations for median value, cut-off value, and validity index [see below, part (E)].

(D) Controls

According to the invention, (D) comprises the steps of (a) providing a reagent containing a recombinantly produced soluble fusion protein comprising the amino acid sequences of (i) one or more soluble carrier polypeptides, (ii) one or more epitopes of PrP(27-30) targeted by the first specific binding agent, and (iii) one or more epitopes of PrP(27-30 targeted by the second specific binding agent; (b) before performing the steps of (A) step (f) and the subsequent workflow, performing the steps of (i) recording the information of the labels of a first amount of control containers of (A) step (a), followed by (ii) providing in the first amount of control containers an aliquot of the homogenization buffer of (A) step (b) step (i), thereby providing negative controls, followed by (iii) correlating the recorded information of (i) with the negative controls, (iv) recording the information of the labels of a second amount of control containers of (A) step (a), followed by (v) providing in the second amount of control containers an aliquot of liquid selected from the group consisting of homogenization buffer lacking the proteolytic enzyme and homogenization buffer additionally containing an effective amount of a protease inhibitor, thereby providing positive controls, followed by (vi) correlating the recorded information of (iv) with the positive controls, followed by (vii) dispensing a measured amount of control reagent into each control container, (viii) including the positive and negative controls in (A) step (f), (B), and (C) steps (a) to (f); (c) performing the steps of (i) repeating (C) step (g) steps (i) to (iii) for each cavity of the detection microwell plate which contains a negative control until the measurement values with regard to all negative controls are processed, (ii) correlating the recorded measurement values of (i) with the information recorded for the negative controls, thereby providing negative control data, (iii) repeating (C) step (g) steps (i) to (iii) for each cavity of the detection microwell plate which contains a positive control until the measurement values with regard to all positive controls are processed, (iv) correlating the recorded measurement values of (iii) with the information recorded for the positive controls, thereby providing positive control data.

In order to facilitate automatic sample tracking, (D) step (b) of the workflow preferably comprises before performing the steps of (A) step (f) and the subsequent steps, performing the steps of (i) reading the information of the labels of a first amount of control containers of (A) step (a) into the computer and storing the information of the respective label into the database, followed by (ii) providing in the first amount of control containers an aliquot of homogenization buffer, thereby providing negative controls, followed by (iii) correlating the stored information of (i) with the negative controls, (iv) reading the information of the labels of a second amount of control containers of (A) step (a) into the computer and storing the information of the respective label into the database, followed by (v) providing in the second amount of control containers an aliquot of homogenization buffer lacking the proteolytic enzyme, thereby providing positive controls, followed by (vi) correlating the stored information of (iv) with the positive controls, followed by (vii) dispensing a measured amount of control reagent into each control container; and (D) step (c) comprises performing the steps of (i) repeating (C) step (g) steps (i) to (iii) for each cavity of the detection microwell plate which contains a negative control until the measurement values with regard to all negative controls are processed, followed by (ii) correlating the stored measurement values of (i) with the information stored for the negative controls, thereby providing negative control data, (iii) repeating (C) step (g) steps (i) to (iii) for each cavity of the detection microwell plate which contains a positive control until the measurement values with regard to all positive controls are processed, followed by (iv) correlating the stored measurement values of (iii) with the information stored for the positive controls, thereby providing positive control data.

To provide a control substance to verify the capability of the first and second binding agent to bind to PrP(27-30), prion protein can be produced recombinantly in a transformed organism. Producing the control substance recombinantly has he advantage that product is non-infective. At the same time, the control substance can be designed such that it is degradable by proteolytic enzymes such as Proteinase K.

Recombinantly produced prion protein has a strong tendency to form insoluble aggregates, particularly at elevated temperatures. For this reason, the invention provides as a control substance a recombinantly produced soluble fusion protein comprising the amino acid sequences of (i) one or more soluble carrier polypeptides, (ii) one or more epitopes of PrP(27-30) targeted by the first specific binding agent, and (iii) one or more epitopes of PrP(27-30 targeted by the second specific binding agent. It was found by the inventors that a fusion protein containing one or more epitopes of PrP(27-30) can be expressed in *coli*, purified and stored without unwanted aggregate formation.

According to the invention, a first preferred soluble carrier polypeptide is a chaperone. Very much preferred is the slyD chaperone of *E. coli* or a fragment thereof. The slyD gene product is a peptidyl prolyl cis-trans isomerase (FKBP-type rotamase). A second preferred soluble carrier polypeptide is a glycine-rich amino acid sequence.

As a very much preferred control substance, the invention provides a protein of the formula S-L1-S-L2-hPrP-His-tag, whereby S is the *E. coli* SlyD chaperone amino acid sequence SEQ ID NO: 1 or a fragment thereof, L1 and L2 are a first and a second glycine-rich linker amino acid sequence, hPrP is a fragment of the human prion preproprotein amino acid sequence according to SEQ ID NO: 3, and His-tag is a histidine tag sequence. Histidine tags are commonly placed on either the N- or the C-terminus of recombinant proteins. Optimal placement of the tag is protein-specific. In principle, it cannot be excluded that the histidine tag may interfere with protein activity (Wu, J. and Filutowicz, M., Acta Biochim. Pol. 46 (1999) 591-599), although the relatively small size and charge of the histidine tag ensure that protein activity is rarely affected. Moving the histidine tag to the opposite terminus (Halliwell, C. M. et al., Anal Biochem. 295 (2001) 257-261) or carrying out the purification under denaturing/renaturing conditions often solves this problem.

Preferably, the protein is a fusion protein. Example 1 illustrates how such a fusion protein can be constructed. Accordingly, very much preferred is a protein according to the invention, characterized in that the protein has the formula S1-L-S2-L-M-hPrP-His-tag, whereby S1 is a fragment of the *E. coli* SlyD chaperone amino acid sequence from position 1 to position 165 according to SEQ ID NO: 1, whereby S2 is a fragment of the *E. coli* SlyD chaperone amino acid sequence from position 1 to position 165 according to SEQ ID NO: 1, L is a linker sequence according to SEQ ID NO: 2, M is a Methionine, hPrP is a fragment of the human prion preproprotein amino acid sequence from position 23 to position 230 according to SEQ ID NO: 3, and His-tag is the histidine tag sequence according to SEQ ID NO: 4.

The fusion protein is an essential component of the control reagent in the assay according to the invention. A preferred method for providing the fusion protein comprises the steps of (a) providing a vector comprising a nucleotide sequence that encodes a fusion protein of the formula S-L1-S-L2-hPrP-His-tag, whereby S is the *E. coli* SlyD chaperone amino acid sequence SEQ ID NO: 1 or a fragment thereof, L1 and L2 are a first and a second glycine-rich linker amino acid sequence, hPrP is a fragment of the human prion preproprotein amino acid sequence according to SEQ ID NO: 3, and His-tag is a histidine tag sequence; (b) transforming a microbial host organism with the vector; followed by (c) cultivating the transformed microbial host organism in a growth medium that contains nutrients, whereby the microbial host strain expresses the fusion protein; followed by (d) purifying the fusion protein from the microbial host strain and/or the growth medium. The skilled person is aware of a large number of expression systems, many of which are available commercially. Well-established expression systems use bacteria or yeast cells as microbial host organisms. Thus, the preferred microbial host organism is a prokaryote or a eukaryote. Bacterial expression systems are frequently based on *E. coli* which is a most preferred microbial host organism. Also most preferred is the method according to the invention, characterized in that the fusion protein has the formula S1-L-S2-L-M-hPrP-His-tag, whereby S1 is a fragment of the *E. coli* SlyD chaperone amino acid sequence from position 1 to position 165 according to SEQ ID NO: 1, whereby S2 is a fragment of the *E. coli* SlyD chaperone amino acid sequence from position 1 to position 165 according to SEQ ID NO: 1, L is a linker sequence according to SEQ ID NO: 2, M is a Methionine, hPrP is a fragment of the human prion preproprotein amino acid sequence from position 23 to position 230 according to SEQ ID NO: 3, and His-tag is the histidine tag sequence according to SEQ ID NO: 4. Preferably, the coding sequence comprises the nucleotide sequence of SEQ ID NO: 5.

It is further preferred that the fusion protein is purified by performing the steps of (i) lysing the microbial host organism, (ii) contacting the lysate of step (i) with a particulate metal chelate affinity matrix capable of binding the histidine tag, thereby immobilizing the fusion protein on the matrix, followed by (iii) washing the matrix, whereby the fusion protein is immobilized on the matrix, followed by (iv) eluting the fusion protein from the matrix, thereby purifying the fusion protein. Thus, purification of histidine tagged fusion protein is facilitated by immobilized metal affinity chromatography. This method is a widely employed method to purify recombinant proteins containing a short affinity-tag consisting of histidine residues (histidine tag). Immobilized metal-affinity chromatography (described by Porath, J. et al., Nature 258 (1975) 598-599) is based on the interaction between a transition metal ion ($Co^{2+}$, $Ni^{2+}$, $Cu^{2+}$, $Zn^{2+}$) immobilized on a particulate metal chelating affinity matrix and specific amino acid side chains. Histidine is the amino acid that exhibits the strongest interaction with immobilized metal ion matrices, as electron donor groups on the histidine imidazole ring readily form coordination bonds with the immobilized transition metal. Proteins containing sequences of consecutive histidine residues are efficiently retained on particulate metal chelating affinity. Following washing of the matrix material, histidine tagged proteins can be easily eluted by either adjusting a low (acidic) pH of the column buffer or by adding free imidazole.

The NTA resin forms a quadridentate chelate and is especially suitable for metal ions with coordination numbers of six, since two valencies remain for the reversible binding of biopolymers. Another material that has been developed to purify histidine tagged proteins is TALON. It consists of a $Co^{2+}$-carboxylmethylaspartate ($Co^{2+}$-CMA), which is coupled to a solid-support resin. TALON has been reported to exhibit less unspecific protein binding than the $Ni^{2+}$-NTA resin, resulting in higher elution product purity (Chaga, G. et al., Biotechnol. Appl. Biochem. 29 (1999) 19-24; Chaga, G. et al., J. Chromatogr. A 864 (1999) 257-256).

For example, $His_6$-tagged proteins such as the fusion protein according to the invention can be bound to $Ni^{2+}$-NTA in low- or high-salt buffers. In the present invention, the immobilization step is preferably performed in the presence of imidazole. Under these conditions, unspecific binding of other Histidine-containing proteins has been found to be reduced. After binding, the target protein can be eluted by e.g., applying a solution with a high concentration of imidazole or applying an imidazole gradient. Washing with a low concentration of imidazole can be used to reduce unspecific binding of microbial host proteins with histidines.

Also preferred, the purified fusion protein is provided as dry matter, e.g., when being part of a kit of parts. To this end, following a change of buffer conditions by, e.g., dialysis, a of the fusion protein can be prepared. Before use the lyophilisate is dissolved again in buffer.

As the skilled person appreciates, the fusion protein according to the invention can be used to test whether a binding agent is capable of forming a complex with prion protein (i.e., a prion protein which shares epitopes with the hPrP portion of the protein according to the invention). Such a test is performed as the positive control in the prion assay according to the invention. Particularly, the invention provides a method of determining whether a binding agent is capable of forming a complex with PrP(27-30) comprising the steps of (a) contacting a protein according to any of the claims _S1 to _S3 with the binding agent, (b) determining whether a complex of the binding agent and the protein has formed, (c) correlating the result to the capability of the binding agent to form a complex with PrP(27-30). It is preferred that before performing step (a), PrP(27-30) is unfolded by the effect of a chaotropic substance. With respect to the receptor or binding agent for PrP(27-30) it is preferred that the binding agent is selected from the group consisting of a polyclonal antibody, a monoclonal antibody, fragments of such antibodies, and genetic constructs comprising the binding domain of an antibody.

The use of a protein (i.e., the fusion protein) according to the invention as a control substance in an assay for determining the presence of PrPc or PrPsc in a biological sample is also part of the invention, likewise the use of a protein according to the invention as a control substance in an assay for quantifying PrPc or PrPsc in a biological sample.

As the data from Example 3 suggest, the protein according to the invention has the potential of being a potent immunogen thereby enabling the induction of highly specific antibodies against hPrP. In view of this finding the use of the protein of the invention for immunizing a mammal is part of the invention. Also, the use of the protein of the invention for producing an antibody against prion protein is part of the invention. In addition, the invention encompasses an injectable pharmaceutical composition for immunization of a mammal, comprising the protein of the invention and a pharmaceutically acceptable carrier. The invention further encompasses a conjugate for immunization of a mammal comprising a protein of the invention and a protein that is immunogenic in the mammal to be immunized.

The invention further provides a kit of parts comprising the protein of the invention, and a binding agent specific for a target selected from the group consisting of PrPc, PrPsc, PrP(27-30) and unfolded PrP(27-30). Very much preferred, the kit of parts additionally comprises a further binding agent specific for a target selected from the group consisting of PrPc, PrPsc, PrP(27-30) and unfolded PrP(27-30). Even more preferred, a kit of parts additionally comprises sample containers, a proteolytic enzyme, buffers, a chaotropic substance, a microwell plate, and a chromogenic substrate.

(E) Classifying the Results

According to the invention, (E) is to be performed after (A), (B), (C), and (D), and comprises the steps of (a) calculating the median of the measurement values of the positive control data [M(p)] provided by (D) step (c); (b) calculating the median of the measurement values of the negative control data [M(n)] provided by (D) step (c); (c) calculating the median of the measurement values of the analysis data [M(a)] provided by (C) step (g); (d) calculating a cut-off value; (e) comparing the measurement value of a tissue sample provided by (C) step (g) with the cut-off value of (d); followed by (f) performing the steps of (i) classifying the measurement value as a positive test result if the measurement value is equal or greater than the cut-off value, or (ii) classifying the measurement value as a negative test result if the measurement value is smaller than the cut-off value, followed by (iii) recording the test result and correlating the test result with the information recorded for the respective tissue sample, followed by (iv) assigning the test result to the respective tissue sample. (g) repeating steps (e) and (f) until the measurement values of all tissue samples are processed.

In order to facilitate automatic sample tracking, (E) step (j) of the workflow preferably comprises performing the steps of (i) classifying the measurement value as a positive test result if the measurement value is equal or greater than the cut-off value, or (ii) classifying the measurement value as a negative test result if the measurement value is smaller than the cut-off value, followed by (iii) storing the test result in the database and correlating the test result with the information stored for the respective tissue sample, followed by (iv) assigning the test result to the respective tissue sample and generating an output which includes the test result and the information of the tissue sample.

Figure 12:
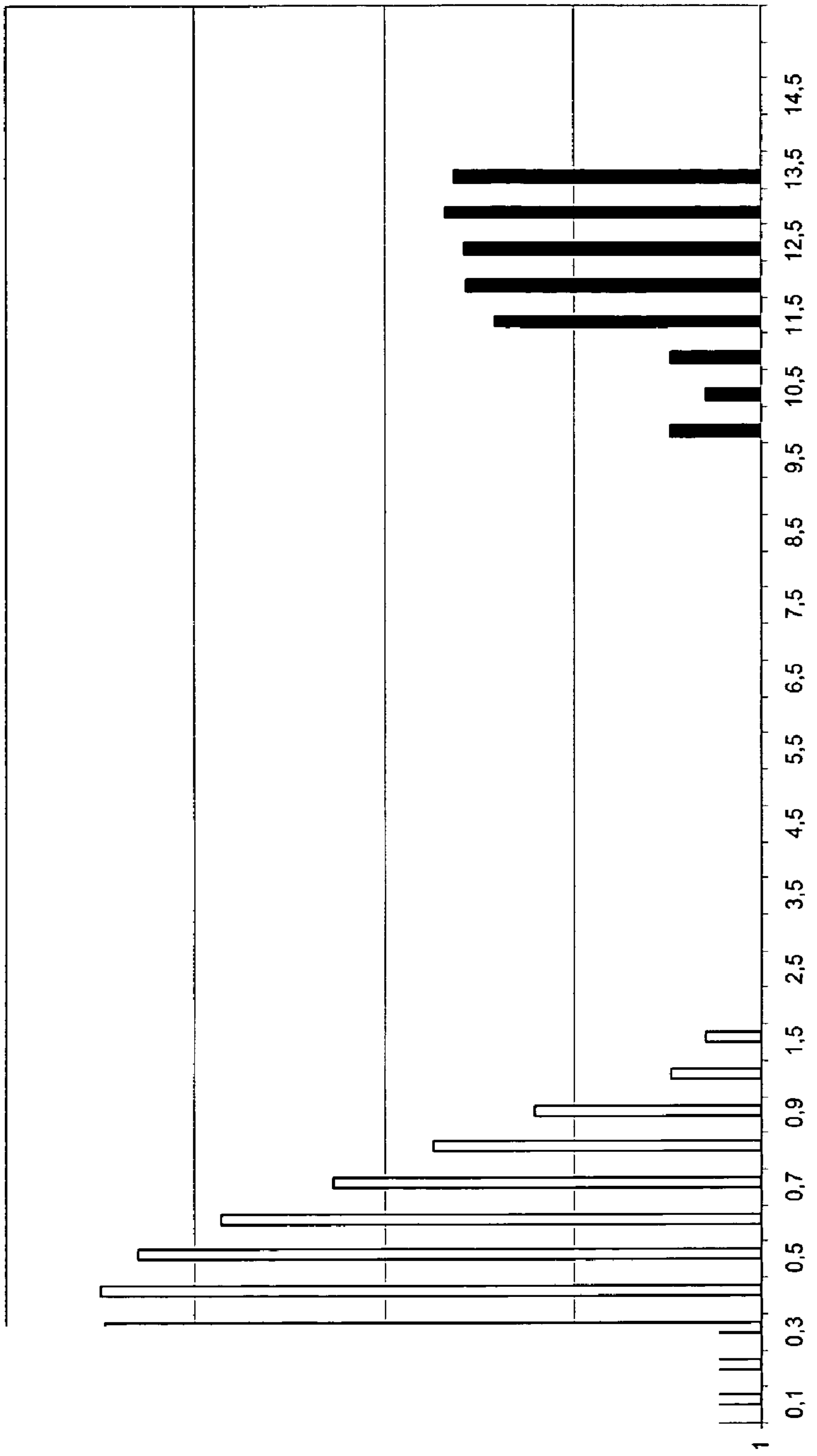
FIG. 12 Diagram illustrating the results of a field study. The high throughput test to determine the presence of PrPsc in a tissue sample taken post mortem from brain was performed in several different laboratories as described in Example 7 and Example 8. For each measurement value derived from a tissue sample a value z=OD [sample]/cut-off value was determined. The x-axis indicates values for "z". The x-axis shows discrete intervals. Calculated values for "z" falling into an interval are grouped as a class for which the member size is indicated on the y-axis. Solid bars indicate the classes obtained with positively tested samples, open bars indicate the classes obtained with negatively tested samples.

Generally, the cut-off value is a means to differentiate measurement values of negative samples from those of positive test samples. A tool to assess the usefulness of a formula for determining a cut-off value is calculating the value "z" by the formula z=OD [sample]/cut-off. For each measurement value derived from a tissue sample a value of z is calculated. The values can be grouped into classes as shown exemplarily in FIG. 12 and the legend thereto. The two distributions shown were found when the cut-off value was calculated as described in Example 8. The distribution resulting from the values for the negative samples is noticeable separated from the distribution resulting from the values for the positive samples. Essentially, the goal of finding a suitable formula for the determination of the cut-off is to prevent the two distributions from overlapping. Rather it is desired to increase the distance of the two distributions.

It is very much preferred that (E) additionally comprises performing a first validity test after step (c) and before step (d) and proceeding with step (d) on the condition that each of (i)

to (iv) is true: (i) M(p) is greater than 1.2, (ii) not more than 25% of the measurement values of the positive controls deviate from M(p) by more than 20%, (iii) M(n) is smaller than 0.2, (iv) not more than 25% of the measurement values of the negative controls deviate from M(n) by more than 20%. It is also very much preferred that (E) step (d) comprises calculating the cut-off value "c1" according to the formula I, $$c1=a\times M(n)+b \quad \text{(I)}$$

whereby "a" is a value between 0.2 and 1 including 0.2 and 1, and "b" is a value between 0.05 and 0.5 including 0.05 and 0.5. Furthermore, it is very much preferred that (E) step (d) additionally comprises calculating a validity index "v1" according to the formula II, $$v1=c1\div M(a) \quad \text{(II)}$$

and proceeding with steps (e) to (g) on the condition that the value of "v1" is between 1.5 and 7 including 1.5 and 7.

It is also preferred that (E) step (d) comprises calculating the cut-off value "c2" according to the formula III, $$c2=y\times M(n)+z\times M(p) \quad \text{(III)}$$

whereby "y" is a value between 1 and 1.5 including 1 and 1.5 and "z" is a value between 0.05 and 0.15 including 0.05 and 0.15. Furthermore, it is preferred that (E) step (d) additionally comprises calculating a validity index "v2" according to the formula IV, and a validity index "v3" according to the formula V, $$v2=M(n)/M(p) \quad \text{(IV)}$$

$$v3=M(a)/M(p) \quad \text{(V)}$$

and proceeding with steps (e) to (g) on the condition that the value of "v2" is below 0.075 not including 0.075 and the value of "v3" is below 0.1 not including 0.1.

The following examples, references, sequence listing and figures are provided to aid the understanding of the present invention, the true scope of which is set forth in the appended claims. It is understood that modifications can be made in the procedures set forth without departing from the spirit of the invention.

SPECIFIC EMBODIMENTS

Example 1

Construction of an Expression Plasmid Comprising Tandem-*E. Coli* SlyD and hPrP(23-230)

On the basis of the pET24a expression plasmid of Novagen (Madison, Wis., USA) the following cloning steps were performed. The vector was digested with NdeI and XhoI and a semi-synthetic cassette according to FIG. 1 with the nucleic acid sequence of SEQ ID NO: 5 comprising tandem-*E. coli* SlyD (also referred to as EcSlyD) and hPrP(23-230) was inserted. As a result, the recombinant expression vector encoded a fusion protein of the formula S-L-S-L-M-hPrP-His-tag, whereby S is a fragment of the *E. coli* SlyD chaperone amino acid sequence from position 1 to position 165 according to SEQ ID NO: 1, L is a linker sequence according to SEQ ID NO: 2, M is a Methionine, hPrP is a fragment of the human prion preproprotein amino acid sequence from position 23 to position 230 according to SEQ ID NO: 3, H is a histidine tag (His-tag) sequence according to SEQ ID NO: 4. The encoded fusion protein is further on also referred to as SS-hPrP(23-230).

Example 2

Purification of the SS-hPrP(23-230) Fusion Protein

Figure 2:
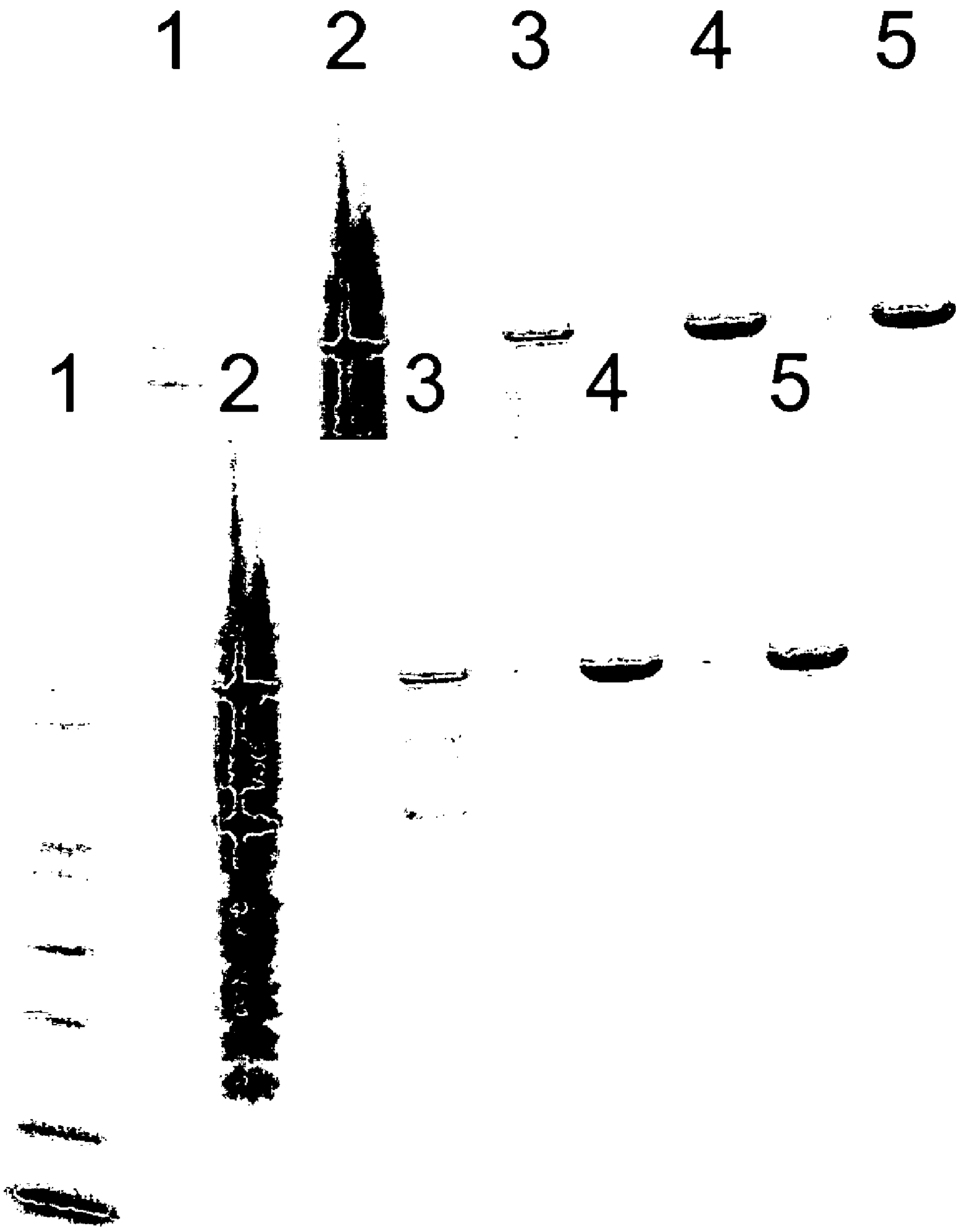
FIG. 2 Purification protocol of SS-hPrP (23-230) as documented by SDS-PAGE. The Coomassie-stained gel shows (1) the protein standard M12 (Novagen), (2) the *E. coli* crude extract, (3) the IMAC flowthrough, (4) the imidazole eluate and (5) the SS-hPrP (23-230) dimer fraction after gel filtration on a Superdex 200 column.

*E. coli* BL21(DE3) cells harboring the expression plasmid of Example 1 were grown in LB medium plus kanamycin to an OD600 of 1, and cytosolic overexpression was induced by adding Isopropyl-beta-D-Thiogalactosid (IPTG) to a final concentration of 1 mM at a growth temperature of 37° C. 4 hours after induction, cells were harvested by centrifugation (20 min at 5,000×g), frozen and stored at −20° C. For cell lysis, the frozen pellet was resuspended in 100 mM sodium phosphate pH 8.0, 7.0 M guanidinium hydrochloride (GuHCl), 10 mM imidazole at room temperature and the resulting suspension was stirred to complete cell lysis for two hours. After centrifugation and filtration, the lysate was applied onto a Ni-NTA (nickel-nitrilo-triacetate) column preequilibrated in the aforementioned lysis buffer. The flowthrough obtained in this step is referred to as the "IMAC flowthrough". After an excessive washing step (>20 column volumes of lysis buffer), the chaotropic lysis buffer was displaced by 50 mM sodium phosphate pH 7.8, 100 mM sodium chloride in order to allow the matrix bound protein to refold (at least 10 column volumes of refolding buffer were applied to ensure residual GuHCl in chaotropic concentrations was removed). The native fusion protein was eluted by applying an elution buffer containing 500 mM imidazole in 50 mM sodium phosphate pH 7.8, 100 mM sodium chloride ("imidazole eluate"). Protein containing fractions were assessed for purity (SDS-PAGE, also see FIG. 2) and pooled. Finally, the protein was subjected to size exclusion chromatography and the dimer fraction was pooled, concentrated and assessed for its spectroscopic properties.

Example 3

UV-Spectroscopic Characterization of the SS-hPrP(23-230) Fusion Protein

Figure 3:
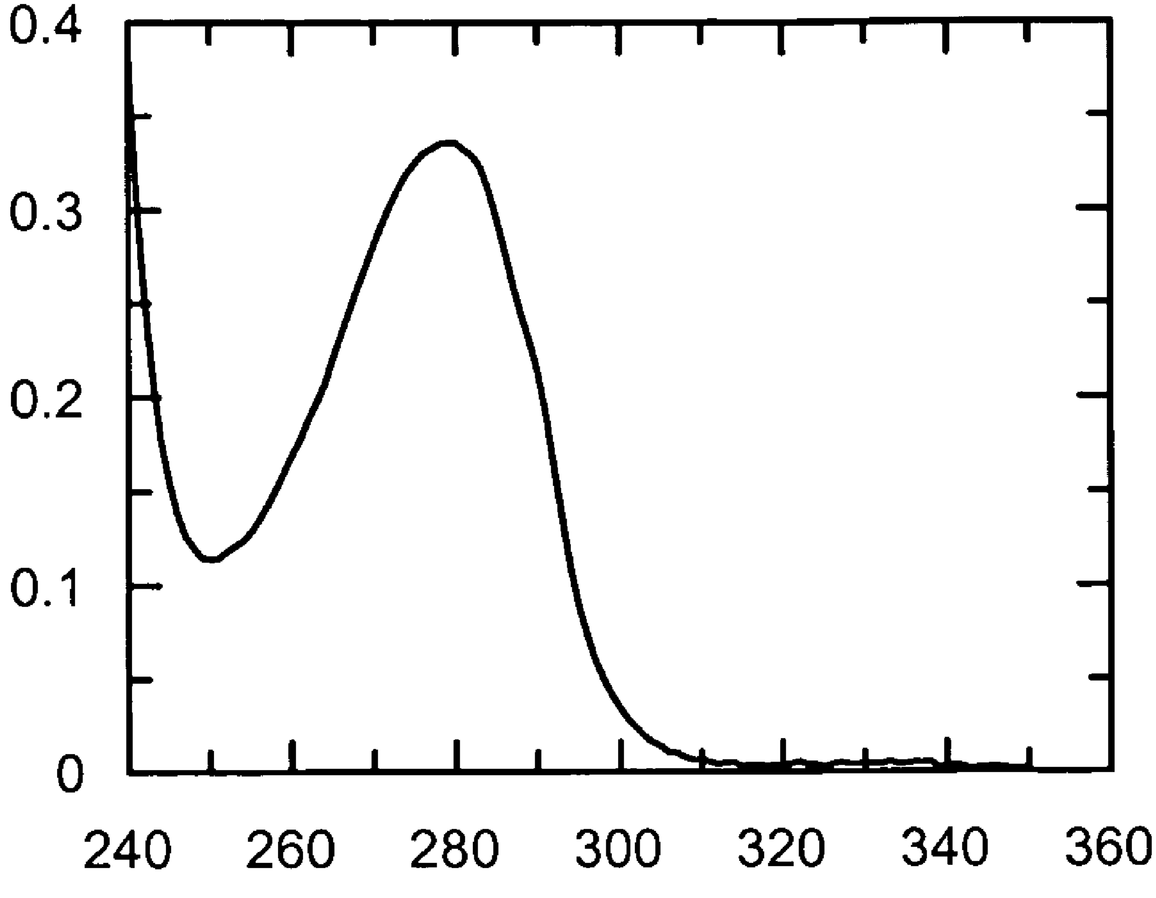
FIG. 3 UV spectrum of the tusion protein SS-hPrP(23-230) after matrix-assisted refolding and imidazole step elution. The ordinate of the diagram indicates absorption values, the abscissa indicates the light wavelength in [nm]. The spectrum was recorded on a Uvicon XS photometer using a pathlength of 1 cm. Buffer conditions were 50 mM sodium phosphate pH 8.0, 100 mM sodium chloride, and about 250 mM imidazole. The shape of the spectrum highlights the remarkable solubility of the chaperoned hPrP(23-230). Stray light effects which would indicate aggregation or association phenomena are not observed.

It was noted that SS-hPrP(23-230) elutes as a soluble protein. The hPrP portion appears to be folded like the native protein. The UV spectra of the recombinantly produced and matrix-refolded fusion protein (see Example 2) do not indicate any aggregation tendency. As shown in FIG. 3, the baseline of the UV-absorption spectrum of SS-hPrp(23-230) in physiological buffer conditions almost equals the abscissa (beyond 310 nm), thus indicating that there are no lightstraying particles resulting from self-association or aggregation phenomena. In contrast, hPrP(23-230) alone displays a considerable aggregation tendency when refolded in the way described in Example 2 (spectra not shown). It was observed that hPrP(23-230) alone forms visible aggregates within hours when incubated in phosphate buffered saline at room temperature.

The shape of the spectrum depicted in FIG. 3 points to a soluble, easy-to-handle polypeptide variant of hPrP(23-230) that should prove useful as a diagnostic tool (e.g., as a protein standard). It might also turn out to be a potent immunogen enabling the induction of highly specific antibodies against hPrP. In short, the method described here facilitates the convenient recombinant production of a soluble variant of the human prion protein in high amounts (yield>10 mg fusion protein/g wet weight). The purity of the fusion polypeptide exceeds 90% after the simple two step chromatography protocol described above. It is noteworthy that comparable results have been found for S-hPrP(23-230), i.e., a fusion protein of the formula S-L-hPrP-H. Thus, the twin chaperone carrier SS as well as the single carrier S confer solubility on the human prion protein (23-230).

Example 4

CD-Spectroscopic Characterization of the SS-hPrP(23-230) Fusion Protein

Figure 4:
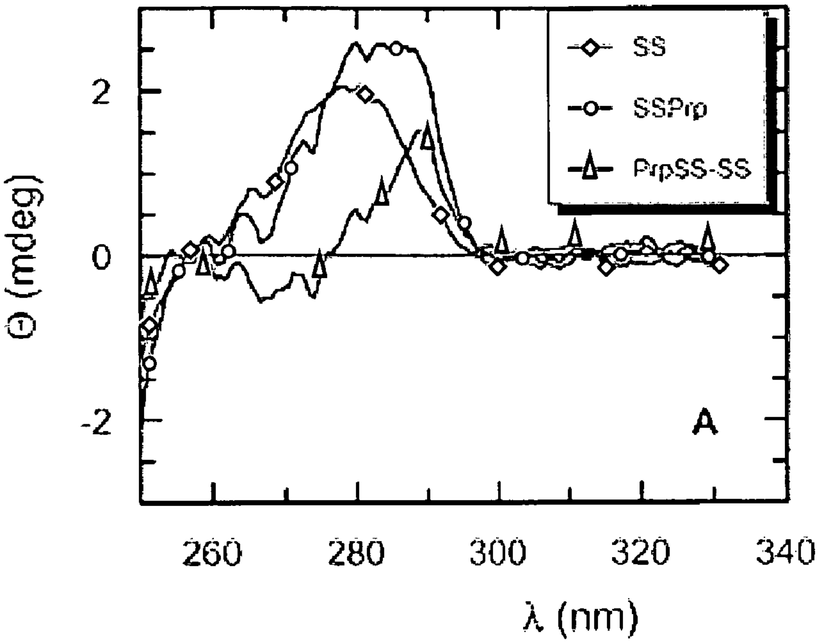
FIG. 4 Differential CD spectroscopy in the near UV region. (A) Near UV CD spectra were recorded for the carrier module SS (diamonds) and the fusion protein SSPrp (circles). Subtraction of the SS spectrum from the SS-hPrP spectrum yields the line indicated by triangles, which is expected to represent the CD signal contribution of the prion part of the fusion protein. (B) When converted into mean residue weight ellipticity, a theoretical hPrP (23-230) spectrum results that is in good agreement with literature data. These results strongly suggest that SlyD(1-165) and human prion protein (23-230) behave as independent folding domains within the context of the fusion protein. Spectra were recorded on a Jasco-720 spectropolarimeter. The path length was 0.5 cm, and the protein concentration of SS and SS-hPrp (23-230) was 33 µM, respectively. Buffer conditions were 50 mM NaP, pH 7.8, 100 mM NaCl, and 1 mM EDTA, and the response was 2 s. The spectra have been accumulated (9×) to improve the signal-to-noise ratio.
Figure 4:
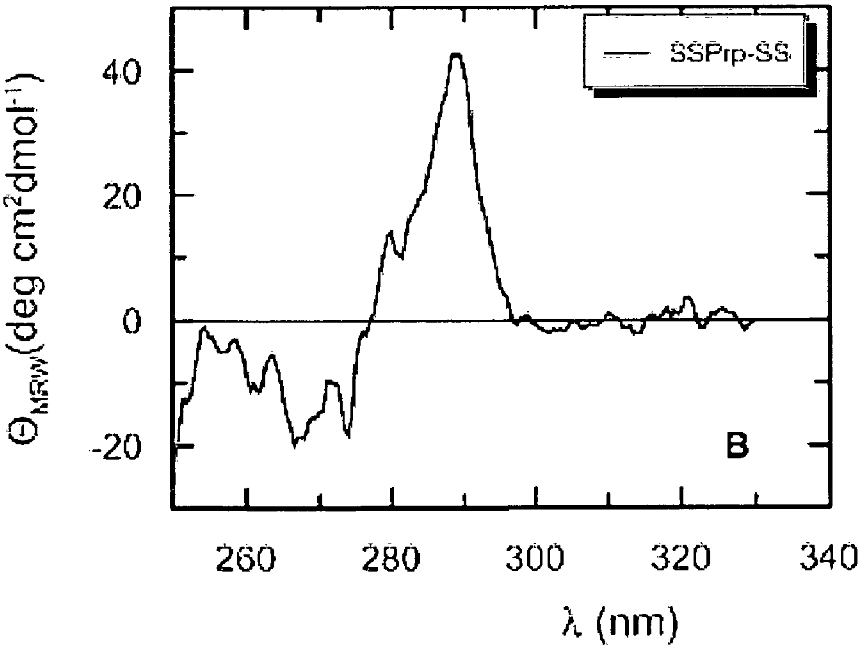

In order to address the question if the hPrP(23-230) portion as part of the fusion protein adopts a native-like fold, near-UV-CD spectra were recorded. Since CD (circular dichroism) signals in the near-UV region (260-320 nm) reflect an ordered molecular surrounding of aromatic residues, near-UV-CD spectra are a convenient probe to characterize globularly folded proteins. Both the carrier module SS [i.e., SlyD(1-165)-($(GGGS)_5$GGG)-SlyD(2-165)] and the complete fusion protein SS-hPrP (23-230) display characteristic CD-signals in the near-UV region (FIG. 4). When the SS carrier signal is subtracted from the SS-hPrP(23-230) signal, the resulting spectrum strongly resembles the typical prion CD-spectra described in the literature (Hornemann et al., FEBS Lett. 413 (1997), 277-281). Thus, the result of this differential spectroscopy experiment provides compelling evidence that hPrP (23-230) is folded native-like in the fusion context, despite the presence of two covalently linked SlyD carrier units. This strongly suggests that the carrier module does not affect the structural integrity of the human prion protein.

Example 5

Thermotolerance of the SS-hPrP(23-230) Fusion Protein

Figure 5A:
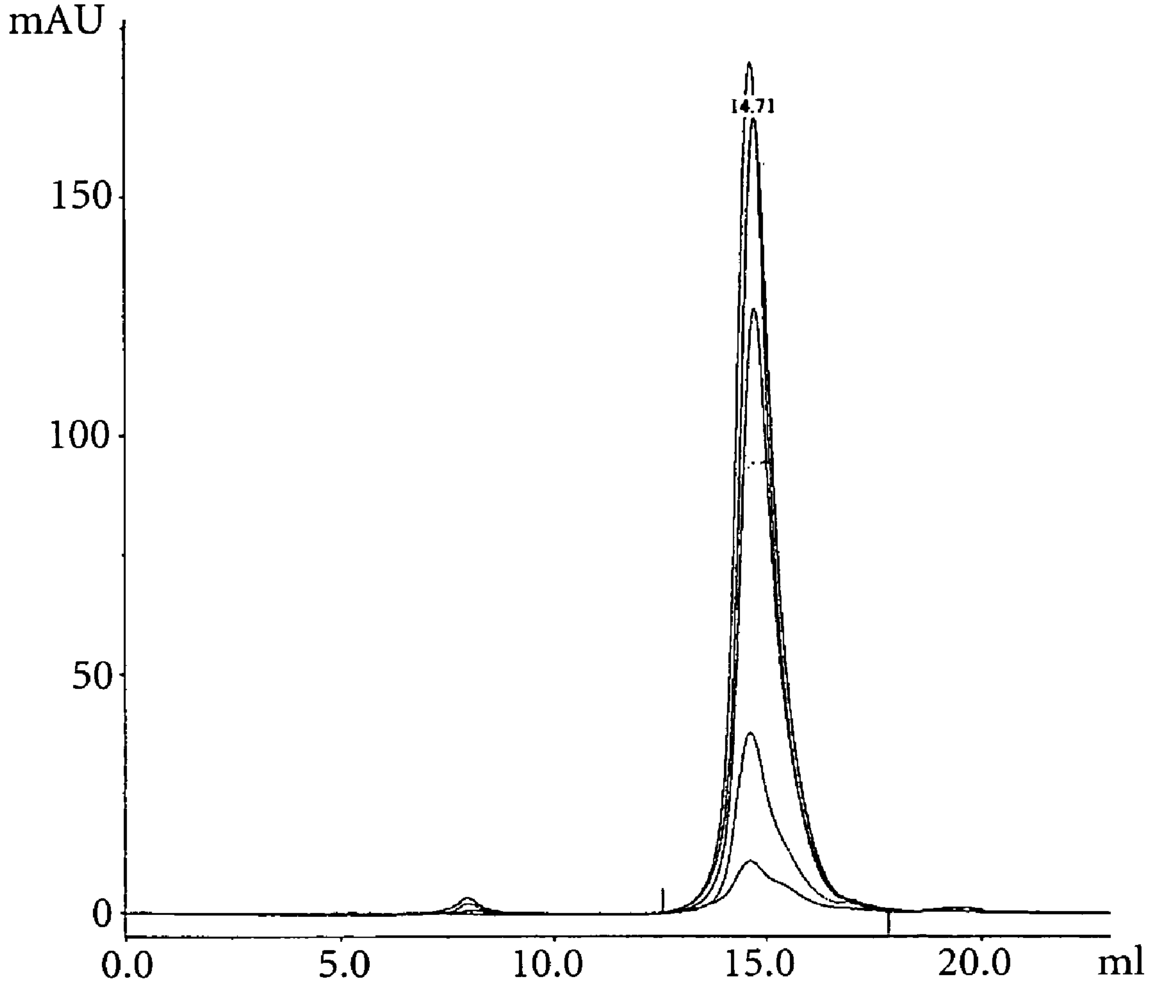
FIG. 5A shows a pronounced aggregation tendency of S-hPrP at temperatures exceeding 45° C. The resulting aggregate particles do not elute from the column, but obviously interact with the Superdex matrix. In contrast, the recovery to SShPrP is very high (FIG. 5B). Moreover, the aggregation tendency is significantly reduced in the twin carrier fusion construct, SS-hPrP.
Figure 5B:
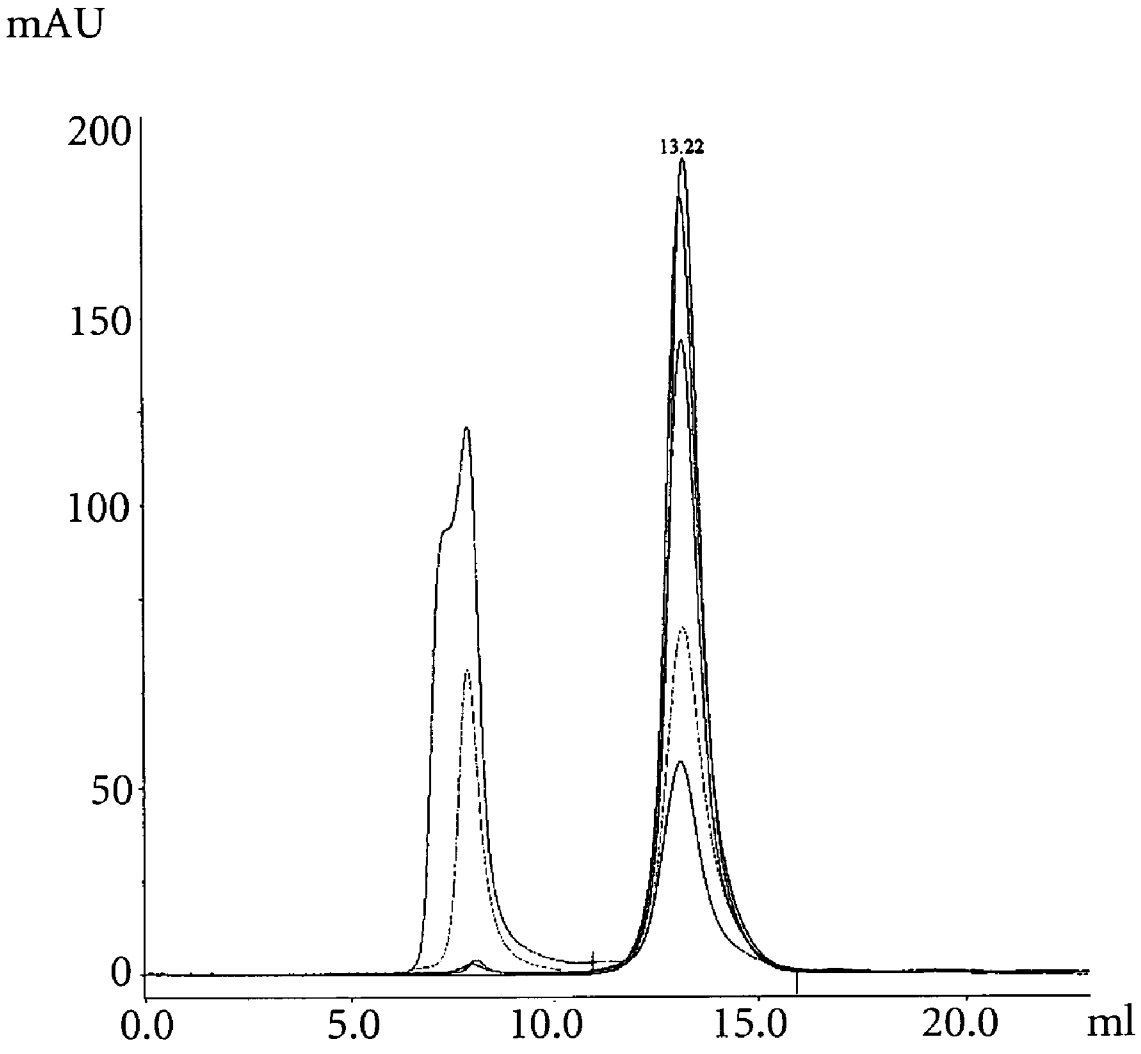
FIG. 5 Different residual solubility of S-hPrP and SS-hPrP after long-time incubation at elevated temperatures. The two fusion proteins were incubated at varying temperatures (from top to bottom: 8° C., 35° C., 45° C., 50° C. and 55° C.) under identical buffer conditions and protein concentrations. Afterwards, they were assessed for aggregate formation by means of FPLC analysis on a Superdex 200 size exclusion column.

In order to address the question if an additional carrier module might enhance the thermotolerance (and thus increase the shelf life) of hPrP(23-230), both SS-PrP [i.e., SlyD(1-165)-($(GGGS)_5$GGG)-SlyD(2-165)-($(GGGS)_5$ GGG)-hPrP(23-230)-His-Tag] and S-PrP [i.e., SlyD(1-165)-($(GGGS)_5$GGG)-hPrP(23-230)-His-Tag] were subjected to thermal stress under identical conditions. Afterwards, both fusion proteins were assessed for their residual solubility by means of FPLC analysis. Pronounced differences were found between SS-hPrP and S-hPrP after long-time-incubation at elevated temperatures. When incubated overnight at temperatures beyond 50° C., S-hPrP precipitates almost quantitatively and there is virtually no more protein detectable in a gel filtration run on a Superdex 200 column (FIG. 5A). When, however, SS-hPrP is pretreated in the same way, the protein recovery after gel filtration is almost quantitative (FIG. 5B). These findings strongly suggest that the additional chaperone carrier module SlyD significantly increases the solubility of the target molecule hPrP(23-230), presumably by supporting the reversibility of thermally induced unfolding. They also point to the conclusion that the two carrier units in the fusion construct SS-hPrP do act cooperatively.

Figure 6:
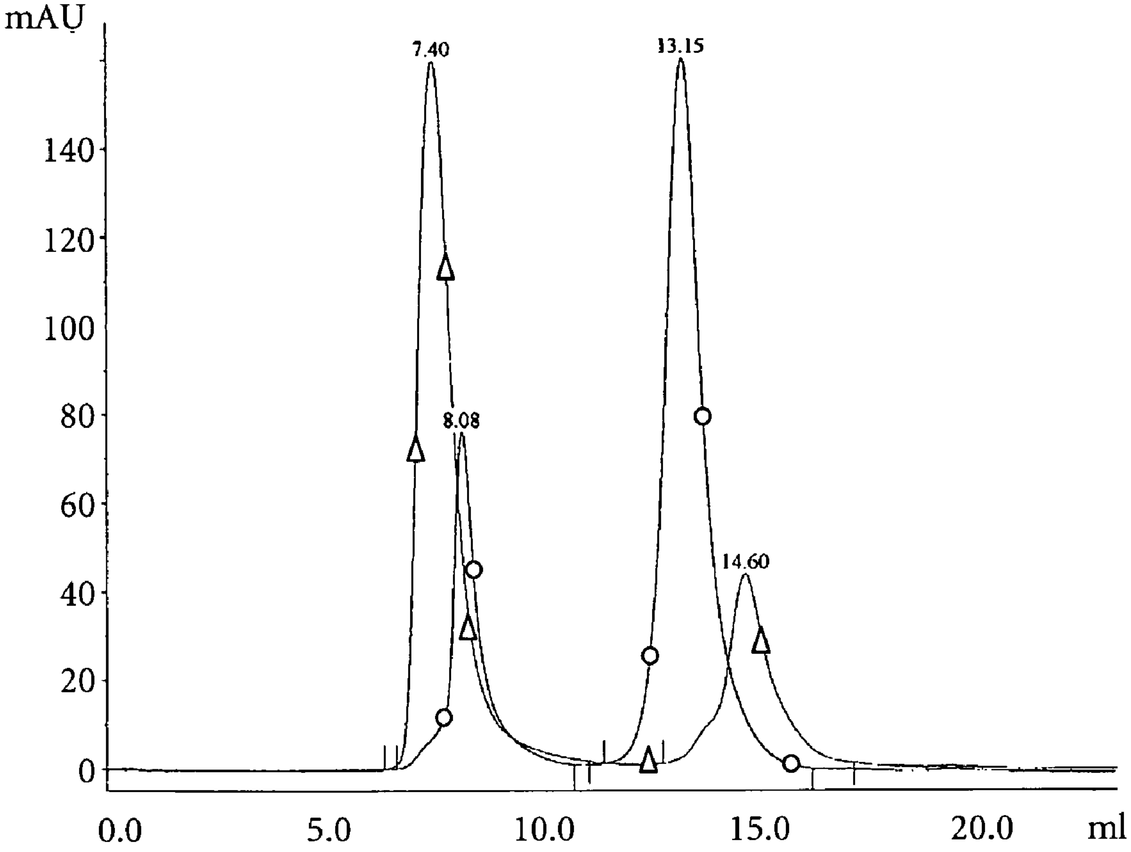
FIG. 6 The chaperone carrier module SS significantly increases the thermotolerance of human prion protein. SS-hPrP and S-hPrP were subjected to thermal unfolding (max. temp. 80° C.) and assessed for their solubility after cooling down to room temperature. Whereas S-hPrP elutes mainly as a high molecular aggregate (line marked by triangles), SS-hPrP elutes chiefly as a soluble dimer (line marked by circles). The result indicates that the SS carrier module increases the reversibility of thermally induced unfolding.

The solubilizing effect of the chaperone carrier is also highlighted after a short-time incubation at elevated temperature: Both SS-hPrP and S-PrP were subjected to thermal unfolding at identical protein concentrations (24 μM each) and buffer conditions. To this end, a 1 cm cuvette was placed in the thermostatable holder and the temperature was raised from 20° C. to 80° C. within a 1 hour run (1° C./min). After cooling down to room temperature, the samples were subjected to FPLC analysis as described and assessed for solubility. It turns out that the main part of S-hPrP elutes as an high molecular aggregate, whereas SS-hPrP elutes chiefly as a soluble dimer (FIG. 6).

This constitutes a significant benefit of both S-hPrP and SS-hPrP as compared to the "unchaperoned" prion protein. In brief, the chaperone fusion constructs of hPrP(23-230) are superior to the unchaperoned protein with respect to thermotolerance and solubility.

Example 7

Prion Assay

A. List of Kit Contents

TABLE 1

| Bottle no./Cap | Label | (a) Content/(b) Function |
|---|---|---|
| 1 colorless | Homogenization Buffer | (a) 100 ml, 3× concentrated, clear solution, foaming possible<br>(b) Homogenization buffer |
| 2a blue | Control Reagent | (a) Approx. 500 ng/ml control substance (recombinantly produced fusion protein) in buffer containing stabilizers,<br>(b) Cut-off control |
| 2b blue | Control Buffer | (a) 8 ml buffer containing preservatives, clear solution<br>(b) Dissolving Control Reagent |
| 2c blue | Control Solution | (a) 25 ml, containing stabilizers and preservatives, foaming possible<br>(b) Cut-off control |
| 3 violet | Digestion Reagent | (a) Recombinantly produced Proteinase K in buffer containing preservatives, red lyophilizate<br>(b) Digestion of PrP |
| 4a green | Stopping Buffer | (a) 40 ml, buffer containing PrP releasing compounds and preservatives (precipitates possible)<br>(b) Dissolving Stopping Reagent |
| 4b green | Stopping Reagent | (a) 3 bottles containing Proteinase K inhibitor, white lyophilizate<br>(b) Stop of Proteinase K digestion and releasing of PrP |
| 5 red | Anti-PrP -Biotin | (a) Monoclonal antibody from mouse, white lyophilizate<br>(b) Capture antibody |
| 6 red | Anti-PrP - Peroxidase (HRP) | (a) Monoclonal antibody from mouse, Fab-fragment conjugated with peroxidase, white lyophilizate<br>(b) Detection antibody |
| 7 red | Incubation Buffer | (a) 80 ml, containing detergent and preservatives, clear solution, foaming possible<br>(b) Antibody incubation buffer |
| 8 white | Washing Buffer | (a) 100 ml, 5× concentrated, containing detergent and preservatives, clear solution, foaming possible<br>(b) Washing Detection Plate |
| 9 black | TMB Substrate Solution | (a) 80 ml, clear solution<br>(b) Detection |
| 10 black | TMB Stop Solution | (a) 20 ml, 0.94 N sulphuric acid, clear solution<br>(b) Detection |
| 11 | Digestion Plate | (a) 3 microplates, round-bottom, white pellet<br>(b) Performing digestion and releasing steps |
| 12 | Detection plate | (a) 3 microplates, 8-well modules in a frame; streptavidin precoated;<br>(b) Detection plate |
| 13 | Sealing film | (a) 15 films<br>(b) sealing digestion and detection plates |

TABLE 1-continued

| Bottle no./Cap | Label | (a) Content/(b) Function |
|---|---|---|
| 14 | Labels for working solutions | (a) 3 labels for each solution (b) Labeling homogenization working solution (1×) and washing buffer (1×) |

BSE := Bovine spongiform encephalopathy;
Fab := fragment antibody binding;
HRP := horse radish peroxidase;
PrP := prion protein B. List of Disposables (a) Tissue cutter (b) Homogenization kit containing racks filled with 96 single, coded (alpha-numeric or 2D-barcode) tubes (containers), each tube filled with 4 homogenization beads; also provided are stopper caps (Capcluster) for sealing during homogenization of the samples, Additional Capcluster are provided for sealing the containers if the samples are to be stored.

(c) Conditioned microplate for digestion/unfolding

C. Preferred Further Equipment (a) Ultrapure water: at least equivalent to Grade 3 water as defined by ISO 3696:1987 (E)

(b) Pipetting means; calibrated pipettes, volumes 10 μl-200 μl (CV <3%), variable volume pipetting means with pipetting tips suitable for 0.1 ml and 0.9 ml (accuracy: <0.5%)

(c) Equipment for sample registration and sample tracking (d) Microplate homogenizer with a speed frequency of at least 30 Hz or 1,800 oscillations per minute.

(e) Microplate centrifuge capable of delivering at least 1000×g and having a swing bucket rotor for 2 deepwell plates.

(f) Microplate incubator (including shaking function): Temperature controlled, shaker accuracy <1.0, Temperature range: 40° C.-50° C., shaking range: at least 700 r.p.m., shaking orbit: at least 1.5 mm.

(g) Microplate shaker: Circular oscillating, shaking orbit: 3 mm, capable of delivering a controlled frequency of 100-1000 r.p.m.

(h) Microplate washer with at least 2 valves, dispense accuracy: ≦4% (300 μl), dispense volume at least 300 μl, cross-wise aspiration: <2 μl/well, adjustable settings of the manifold.

(j) Microplate reader, photometric; standard filter (450 nm and 620 nm) or continuous filter (400 nm-700 nm), measuring range: 0-4.000 Abs, resolution: 0.001 Abs, standard interface to computer.

(k) Roller, 30-50 r.p.m.

(l) Calculation software recommended (m) Automated system

D. Preparation of Working Solutions

Only ultrapure water at 22 (room temperature: RT) has to be used for the dilutions. For the reconstitution of the lyphilizates a roller has to be used.

TABLE 2

| Working solution | Reconstitution/Preparation of working solution |
|---|---|
| Homogenization Buffer Solution 1 | Dilute the content of bottle 1 with 200 ml ultrapure water at 22° C. ± 5° C. and mix thoroughly to homogeneity. |
| Control Reagent Solution2a | Reconstitute the lyophilizate in 6 ml control buffer (bottle 2b) at 22° C. ± 5° C. and mix (minimum 15 min) thoroughly to a clear solution. |
| Control Buffer Solution2b | Ready-to-use solution, raise temperature to 22° C. ± 5° C. before usage. |
| Control Solution Solution 2c | Ready-to-use solution, raise temperature to 22° C. ± 5° C. before usage. |
| Digestion Reagent Solution 3 | Reconstitute the lyophilizate in 10 ml ultrapure water at 22° C. ± 5° C. and mix thoroughly at least 5 min to a clear, red solution. |
| Stopping Buffer Solution 4a | Raise temperature to 22° C. ± 5° C., dissolve precipitates by mixing for at least 30 min to a clear, colorless solution. |
| Stopping Reagent Solution 4b | Reconstitute the lyophilizate in 12 ml of stopping buffer (solution 4a) at 22° C. ± 5° C., and mix thoroughly to a clear, colorless solution. |
| Anti-PrP-Biotin Solution 5 | Reconstitute the Iyophilizate in 1 ml ultrapure water at 22° C. ± 5° C., and mix thoroughly to a clear, colorless solution. |
| Anti-PrP-Peroxidase Solution 6 | Reconstitute the lyophilizate in 1 ml ultrapure water at 22° C. ± 5° C., and mix thoroughly to a clear, colorless solution. |
| Incubation Buffer Solution 7 | Ready-to-use solution, raise temperature to 22° C. ± 5° C. before usage; slightly opalescent, colorless solution. |
| Washing Buffer Solution 8 | Dilute the content of bottle 8 with 400 ml of ultrapure water at 22° C. ± 5° C. and mix thoroughly |
| TMB Substrate Solution Solution 9 | Ready-to solution, raise temperature to 22° C. ± 5° C. before usage. |
| TMB Stop Solution Solution 10 | Ready-to solution, raise temperature to 22° C. ± 5° C. before usage. |
| Homogenization Solution Solution 11 | For 96 cavities: Add 3 ml reconstituted digestion reagent (solution 3) to 97 ml homogenization buffer (solution 1), and mix to homogeneity at 22° C. ± 5° C. resulting in a clear, pink solution. |
| Detection Solution Solution 12 | For 96 cavities: Add 0.3 ml reconstituted anti-PrP-HRP (solution 6) and 0.3 ml of anti-PrP-biotin (solution 5) to 25 ml incubation buffer (solution 7), and mix gently for at least 15 min resulting in a slightly opalescent solution. |

The test is designed for use of fresh, frozen and autolyzed sample material. Samples must not contain clotted blood. The controls are performed simultaneously with each microplate. All samples arc tested in a single analysis. Preferably, calculation software is used to evaluate the samples.

E. Pipetting Scheme for the Microplate

The preferred pipetting scheme for a 8×12 microplate is given by Table 3 which is a representation of the layout of the cavities of a 8×12 microwell plate or a rack with containers in the 8×12 format.

TABLE 3

| | 1 | 2 | 3 | 4 | 5 | 6 | 7 | 8 | 9 | 10 | 11 | 12 |
|---|---|---|---|---|---|---|---|---|---|---|---|---|
| A | C+ | C− | S1 | | | | | | | | | |
| B | C+ | C− | S2 | | | | | | | | | |
| C | C+ | C− | S3 | | | | | | | | | |
| D | C+ | C− | | | | | | | | | | |
| E | C+ | C− | | | | | | | | | | |

TABLE 3-continued

| | 1 | 2 | 3 | 4 | 5 | 6 | 7 | 8 | 9 | 10 | 11 | 12 |
|---|---|---|---|---|---|---|---|---|---|---|---|---|
| F | C+ | c− | | | | | | | | | | S78 |
| G | C+ | C− | | | | | | | | | | S79 |
| K | C+ | C− | | | | | | | | | | S80 |

Key:
C+ = Control positive;
C− = Control negative;
S1–S80 = Samples 1–80

F. Sample Material

In the abattoir the sample from the brain stem (Medulla oblongata) is collected through the foramen magnum (skull opening towards the spinal cord) using a specially designed spoon. The sample is stored in a transport container, closed tightly and labeled appropriately for absolutely unambiguous identification and then transferred to the lab. In the laboratory each sample is registered in a database and labeled.

G. Homogenization

The homogenization steps are performed according to the protocol given in Table 3.

TABLE 4

| Step | Action | Amount/ well | Time/ Tempera- ture |
|---|---|---|---|
| 1 | Pipette homogenization solution 1× (solution 11) in all tubes (column 2-12) of the homogenization plate (see pipetting scheme). | 0.9 ml | RT |
| 2 | Pipette control solution (solution 2c) in all tubes (column 1) of the homogenization plate (see Table 3). | 0.9 ml | RT |
| 3 | Open the container in a safety cabinet and put the Medulla oblongata on a pad. Cut once a defined piece of obex and put it into one tube of the homogenization plate of column 3-12 (according to Table 3). | 150 ± 30 mg | RT |
| 4 | Pipette control reagent (solution 2a) in all tubes of column 1-2 (see Table 3). | 100 µl | RT |
| 5 | Cover all the tubes of the plate tightly with the Capcluster and clamp it on the homogenization instrument in the appropriate position. The sample is stable at RT for up to 60 min. | | RT |
| 6 | Homogenize at maximum speed (30 Hz). | | 5 min RT |
| 7 | Detach the plate, turn 180° and clamp it again to the sample plate. | | |
| 8 | Homogenize at maximum speed (30 Hz). | | 5 min RT |
| 9 | Detach the plate from homogenizer and transfer it to the microplate centrifuge. Centrifuge at 1000 × g. | | 2 min RT |

RT = room temperature, 22° C. ± 5° C.

H. Digestion

| Step | Action | Amount/ well | Time/ Tempera- ture |
|---|---|---|---|
| 10 | Remove the caps and transfer controls and homogenates to the digestion plate. Tightly close the homogenization plate tubes with Capcluster and store. | 150 µl | RT |
| 11 | Tighten the digestion plate with a sealing film and place on a running shaker (600 r.p.m. ± 50 r.p.m.) under constant humidity. | | RT 14 ± 2 min |
| 12 | Transfer the digestion plate on a running, shaking incubator (700 r.p.m. ± 50 r.p.m.) under constant humidity. | | 42 ± 2° C. 30 ± 2 min |
| 13 | Add stopping reagent (solution 4b) to each well, mix 3× by pipetting up and down and tighten the plate with a sealing film. Incubate on a shaker (400 ± 50 r.p.m.) under constant humidity. | 100 µl | RT 20 ± 2 min |

J. Detection

The detection steps are performed as given in Table 4.

| Step | Action | Amount/ well | Time/ Tempera- ture |
|---|---|---|---|
| 14 | Pipette aliquots from each well of the digestion plate into the corresponding wells of the detection plate according to the pipetting scheme. | 40 µl | RT |
| 15 | Pipette detection solution (solution 12) into each well of the detection plate, mix at least once and tighten the plate with a sealing film. incubate on a shaker (400 ± 50 r.p.m.) under constant humidity. | 200 µl | RT 60 ± 5 min |
| 16 | Remove the solution from each well by aspiration or tapping. Wash 3 times with washing buffer solution (solution 8). | 3 × 300 µl | RT |
| 17 | Add TMB substrate solution (solution 9) and tighten the plate with sealing film. Incubate on a shaker (400 ± 50 r.p.m.) under constant humidity | 200 µl | RT 10 ± 2 min |
| 18 | Add TMB stop solution (solution 10) | 50 µl | RT |
| 19 | Place detection plate into the microplate reader within 10 min and mix for 10 s. Measure absorbance at 450 nm (subtract absorbance at 620 nm). | | RT 10 s |
| 20 | Save the primary data unmodifiable on a Computer. | | |

Example 8

Cut-Off Calculation and Interpretation of Measured Data

A. Data Setting

The absorbance values of the control negative are used to calculate the medians used for setting the cut-off value. The median for the samples and the control positive is used to verify the test function.

| Step | Action |
|---|---|
| Calculation of the median values | |
| 1 | Calculate the median for the 8 control positives (column A-H). |
| 2 | Calculate the median for the 8 control negatives (column 2, row A-H). |
| 3 | Calculate the median for all samples (n ≧ 8) (columns 3-12, row A-H). |
| Check of the medians for validity | |
| 4 | a) The median tor the positive controls has to be above OD 1.2.<br>b) Only two values out of 8 positive controls are accepted with a deviation from the median of more than 20%.<br>c) The median tor the negative controls has to be below OD 0.2.<br>d) Only two values out of 8 negative controls are accepted with a deviation from the median of more than 20%. |
| 5 | If the validity requirements have not been met, the test has to be repeated. |

For data interpretation at least 8 samples are analyzed on one microplate. For evaluation purposes it is necessary that the number of expected negative samples is higher than the expected number of positive samples. OVER-readings are interpreted as OD 4.0.

B. Calculation of the Cut-Off Value

The median of the control negative is used to calculate the cut-off value.

| Step | Action |
|---|---|
| 6 | Calculate the cut-off value "c" by the formula: c = 0.5 × median control negative + OD 0.25 |
| 7 | This cut-off value has to be verified by applying the following procedure. |
| | Check the plausibility of the cut-off by using the median ot the samples and the cut-off value. |
| 8 | Divide the cut-off value by the median for all samples. |
| 9 | The cut-off is verified and the test performance is acceptable if the quotient obtained in step 8 is between 1.5 and 7. |
| 10 | If only one of the above criteria has not been matched, the plate is not valid and the test has to be repeated. |

C. Assessment of Reactive Samples

Each sample found to be above the cut-off is assessed as initially reactive, i.e., has a positive test result.

| | Action |
|---|---|
| 11 | Compare the values of the samples to the cut-off. |
| 12 | Select those which are equal to, or above the cut-off. |
| 13 | Label these as reactive (positive test result). |

Preferably, initially reactive samples are retested in duplicate. For retesting and data interpretation at least 8 samples are analysed on a retest plate. For cut-off calculation it is necessary, that the number of expected negative samples is higher than the expected number of positive samples. The homogenates in the relevant sample containers are mixed gently and centrifuged at 1,000×g for 2 min. The digestion steps according to Example 7 H and the detection steps according to Example 7 J are performed with the homogenate and with freshly prepared controls. The whole procedure is performed in duplicate. If two out of three tests for an initially reactive sample are retested reactive, the sample is labeled as repeated reactive.

D Documentation of Data

Preferably, the test is carried out under controlled conditions and all data produced during test implementation are documented, i.e., recorded. In particular, the traceability, from sampling to result, is documented without any deviation. Raw data are stored in such a way that every document change is transparent. To ensure compliance with these requirements, an appropriate quality management system is very much preferred, eg., according to EN ISO/IEC 17025:2000.

Example 9

Reactivity of Positive and Negative Controls, Cut-Off Value Determination

Figure 7:
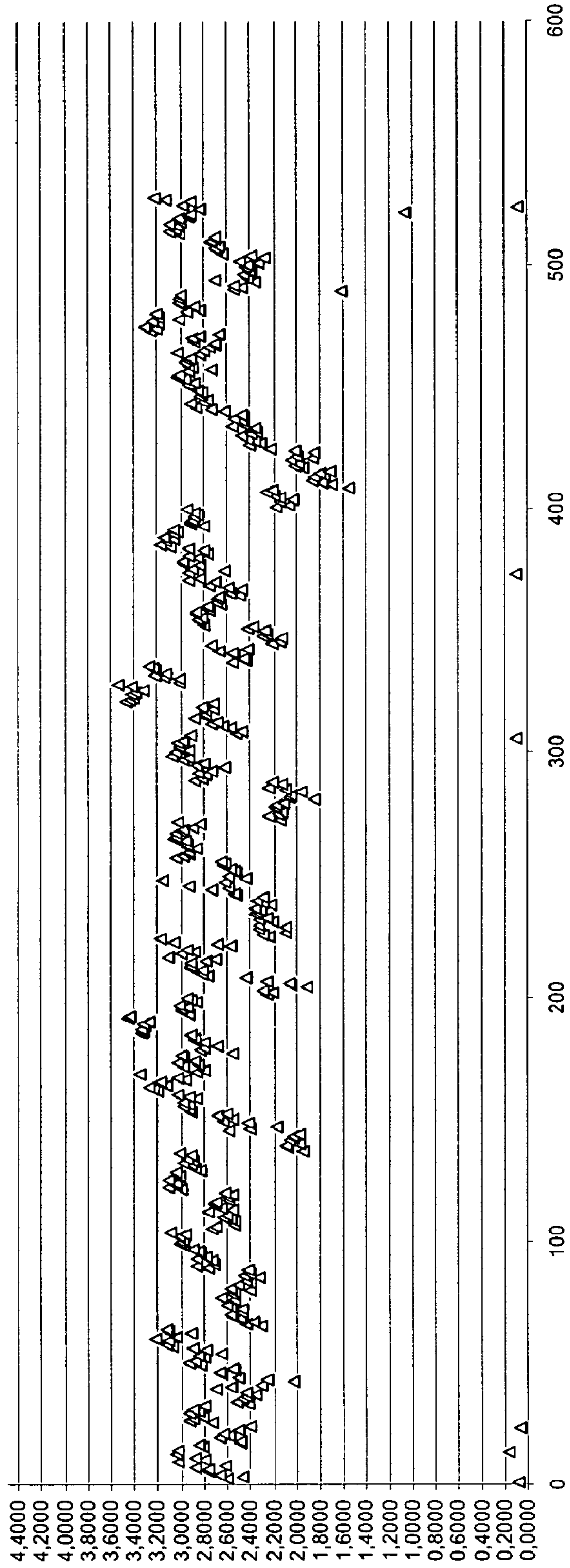
FIG. 7 High throughput test to determine the presence of PrPsc in a tissue sample taken post mortem from brain as described in Example 7; I: Measurement values obtained for the positive controls. Each measurement is represented by a triangle. The x-axis of the diagram indicates the plate number, the y-axis indicates OD values.
Figure 8:
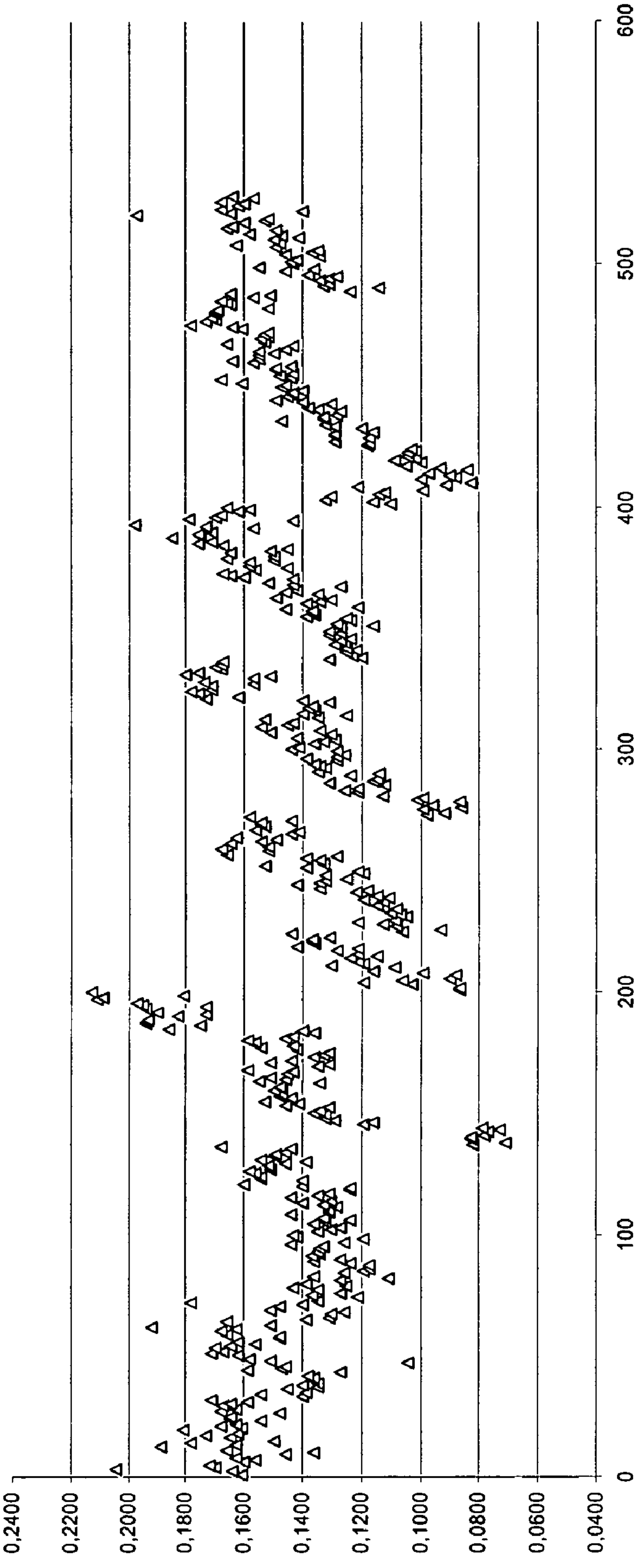
FIG. 8 High throughput test to determine the presence of PrPsc in a tissue sample taken post mortem from brain as described in Example 7; II: Measurement values obtained for the negative controls. Each measurement is represented by a triangle. The x-axis of the diagram indicates the plate number, the y-axis indicates OD values.
Figure 9:
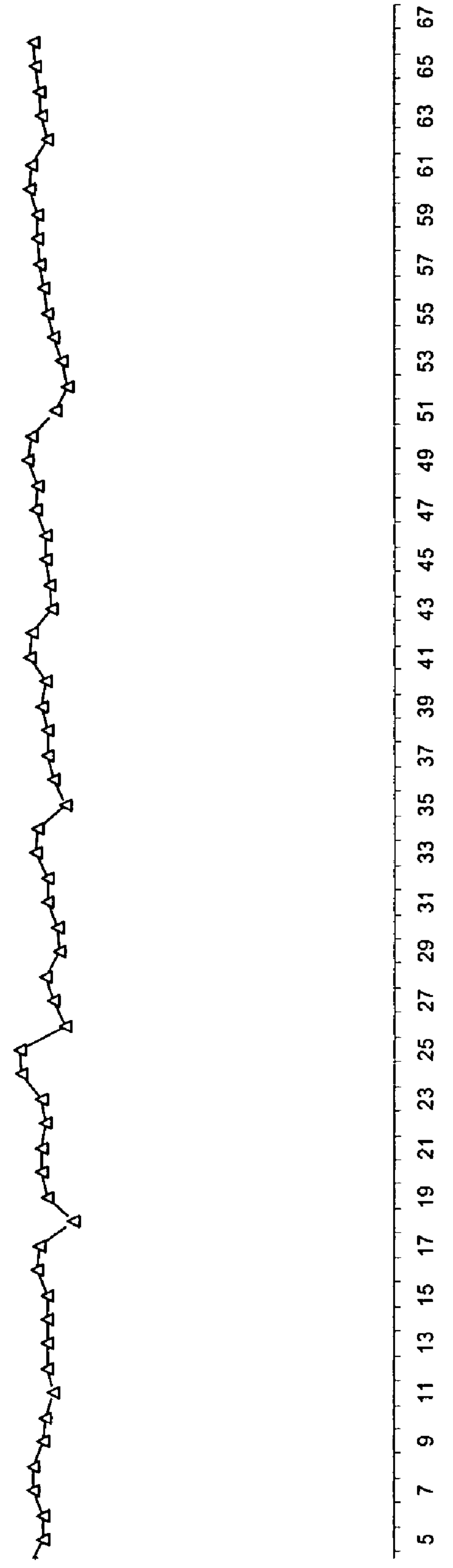
FIG. 9 High throughput test to determine the presence of PrPsc in a tissue sample taken post mortem from brain as described in Example 7 and Example 8; III: Cutoff values calculated according to Example 8. Each measurement is represented by a triangle. The x-axis of the diagram indicates the plate number, on a logarithmic scale the y-axis indicates the cut-off values.
Figure 10:
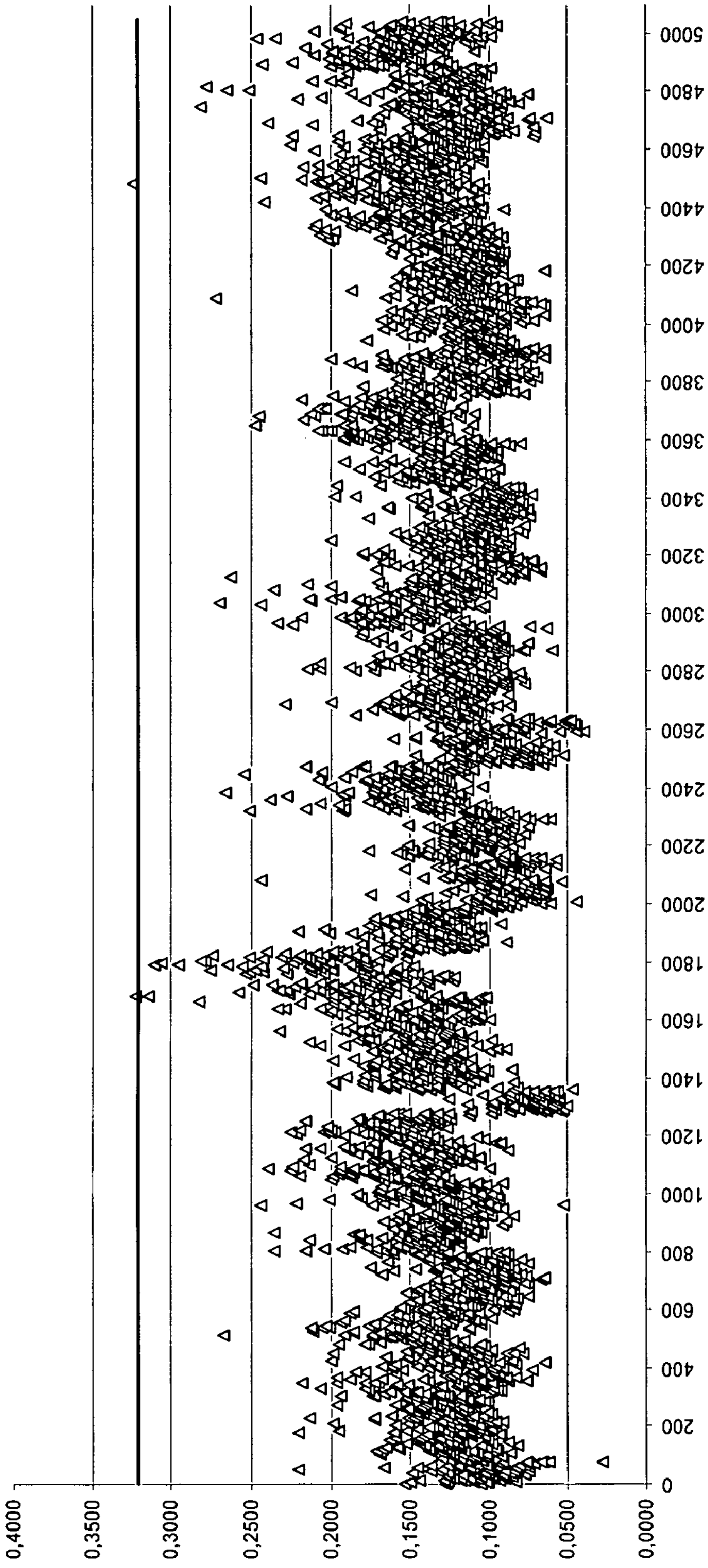
FIG. 10 High throughput test to determine the presence of PrPsc in a tissue sample taken post mortem from brain as described in Example 7 and Example 8; VI: The diagram shows measurement values obtained with tissue samples from cattle which had been tested using a reference test system with a negative result. The reference test system had official approval by the European Union. Each measurement value is represented by a triangle. The x-axis of the diagram indicates the sample number, the y-axis indicates OD values. The solid line indicates the cut-off value.
Figure 11:
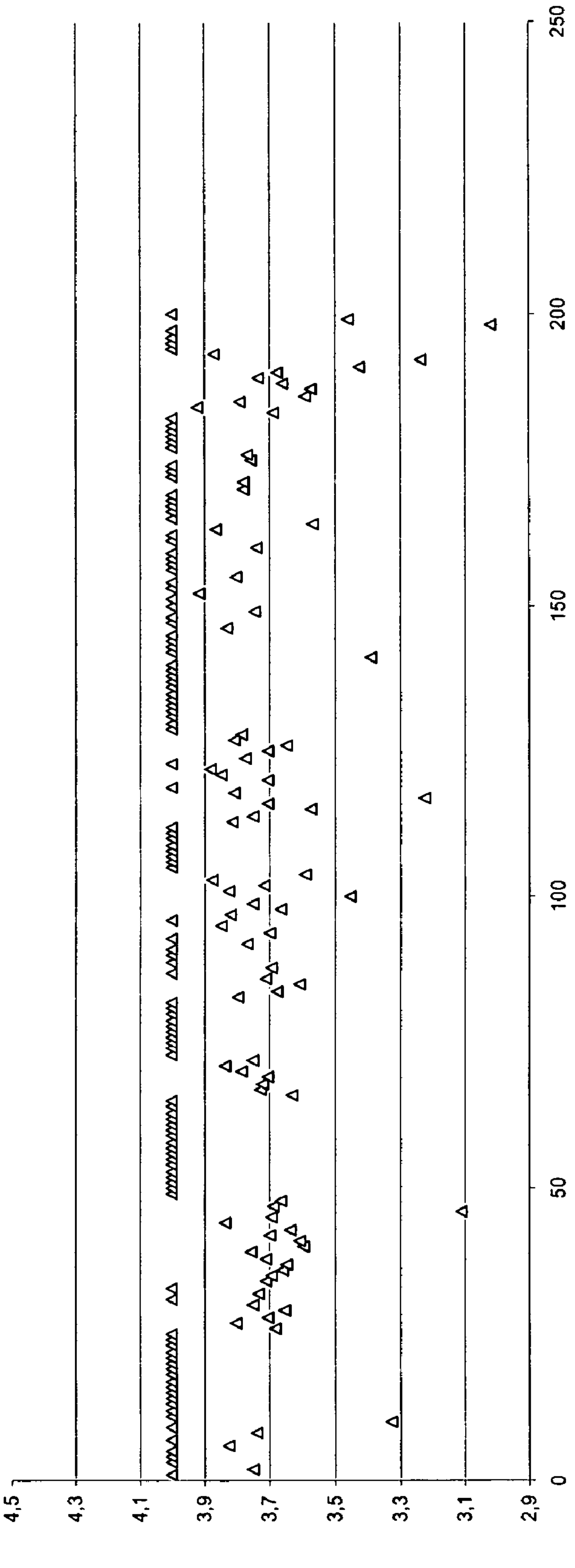
FIG. 11 High throughput test to determine the presence of PrPsc in a tissue sample taken post mortem from brain as described in Example 7 and Example 8; V: The diagram shows measurement values obtained with tissue samples from cattle which had been tested using a reference test system with a positive result. The reference test system had official approval by the European Union. Each measurement value is represented by a triangle. The x-axis of the diagram indicates the sample number, the y-axis indicates OD values. Over-readings are given as OD 4.0 as described in Example 8.

The assay as described in Example 7 and Example 8 was performed in three professional laboratories. Positive and negative controls were performed and measured values were recorded. FIGS. 7 and 8 are a graphical representation of the measured values for the controls. FIG. 9 is a graphical representation of the cut-off values obtained.

What is claimed is:

1. A method for preparing a biological sample suspected of containing PrPsc such that it is suitable for specific detection of PrPsc, said method comprising the steps of:

homogenizing the sample using spherical beads, wherein each bead weighs between 50 mg and 100 mg;

transferring a liquid fraction of the homogenate to a microwell plate, wherein said microwell plate comprises a coating of chaotropic agent, the coating comprising a mixture of a pre-determined amount of a chaotropic agent to partially denature PrPsc and water-soluble carbohydrate dried onto the interior surfaces of each well;

digesting the homogenated fraction in the microwell plate with proteinase K, whereby PrPc present in the sample is digested and PrPsc present in the sample is partially digested but wherein a protease-resistant fragment of PrPsc present in the sample remains folded and undigested; and adding an unfolding reagent comprising a peptidic protease inhibitor to inhibit protease K activity and additional chaotropic agent to the digested homogenated fraction, wherein the additional chaotropic agent is guanidine hydrochloride and whereby the additional chaotropic agent achieves a final concentration of chaotropic agent sufficient to unfold the fragments of protease-resistant PrPsc present in the sample, thereby obtaining a biological sample suitable for specific detection of PrPsc.

2. The method of claim 1, wherein the peptidic protease inhibitor is a trypsin inhibitor.

3. The method of claim 2, wherein the peptidic protease inhibitor is selected from the group consisting of trypsin inhibitor from soybean and trypsin inhibitor from egg white.

4. The method according to claim 3, wherein the peptidic protease inhibitor is trypsin inhibitor from egg white.

* * * * *